US009469685B2

(12) United States Patent
Ahmed et al.

(10) Patent No.: US 9,469,685 B2
(45) Date of Patent: Oct. 18, 2016

(54) ANTIBODIES DIRECTED AGAINST INFLUENZA

(75) Inventors: Rafi Ahmed, Atlanta, GA (US); Jens Wrammert, Decatur, GA (US); Patrick C. Wilson, Chicago, IL (US)

(73) Assignees: Emory University, Atlanta, GA (US); The University of Chicago, Chicago, IL (US)

( * ) Notice: Subject to any disclaimer, the term of this patent is extended or adjusted under 35 U.S.C. 154(b) by 0 days.

(21) Appl. No.: 13/978,607

(22) PCT Filed: Jan. 10, 2012

(86) PCT No.: PCT/US2012/020824
§ 371 (c)(1),
(2), (4) Date: Jul. 8, 2013

(87) PCT Pub. No.: WO2012/096994
PCT Pub. Date: Jul. 19, 2012

(65) Prior Publication Data
US 2014/0046039 A1     Feb. 13, 2014

Related U.S. Application Data

(60) Provisional application No. 61/431,406, filed on Jan. 10, 2011.

(51) Int. Cl.
| C07K 16/10 | (2006.01) |
| C12N 7/00 | (2006.01) |
| A61K 39/00 | (2006.01) |

(52) U.S. Cl.
CPC ..... *C07K 16/1018* (2013.01); *A61K 2039/505* (2013.01); *C07K 2317/21* (2013.01); *C07K 2317/33* (2013.01); *C07K 2317/76* (2013.01); *C07K 2317/92* (2013.01)

(58) Field of Classification Search
None
See application file for complete search history.

(56) References Cited

PUBLICATIONS

Wrammert et al. (Nature, 2008, p. 667-672).*
Cori et al. (Science, 2011, vol. 333, p. 850-856).*
Hashem (Biomed Research International, 2015, p. 1-13).*
Wrammert et al. (JEM, Jan. 17, 2011).*
Li et al. (PNAS, Jun. 2012, vol. 109, p. 9047-9052).*
Beigel, J., (2008), "Influenza.", Critical Care Medicine, 36(9): 2660-2666.
Bernasconi et al., (2002), "Maintenance of Serological Memory by Polyclonal Activation of Human Memory B Cells.", Science, 298(5601): 2199-2202.
Brockwell-Staats et al., (2009), "Diversity of influenza viruses in swine and the emergence of a novel human pandemic influenza A (H1N1).", Influenza and Other Respiratory Viruses, 3(5): 207-213.
Brokstad et al., (1995), "Parenteral Influenza Vaccination Induces a Rapid Systemic and Local Immune Response.", Journal of Infectious Diseases, 171(1): 198-203.
Corti et al., (2010), "Heterosubtypic neutralizing antibodies are produced by individuals immunized with a seasonal influenza vaccine.", The Journal of Clinical Investigation, 120(5): 1663-1673.
Crotty et al., (2003), "Cutting Edge: Long-Term B Cell Memory in Humans after Smallpox Vaccination.", The Journal of Immunology, 171(10): 4969-4973.
Dawood et al., (2009), "Emergence of a Novel Swine-Origin Influenza A (H1N1) Virus in Humans.", New England Journal of Medicine, 360(25): 2605-2615.
De Wildt et al., (2000), "Comparable heavy and light chain pairings in normal and systemic lupus erythematosus IgG + B cells.", European Journal of Immunology, 30(1): 254-261.
Duty et al., (2009), "Functional anergy in a subpopulation of naive B cells from healthy humans that express autoreactive immunoglobulin receptors.", The Journal of Experimental Medicine, 206(1): 139-151.
Ehrenmann et al., (2010), "IMGT/3Dstructure-DB and IMGT/DomainGapAlign: a database and a tool for immunoglobulins or antibodies, T cell receptors, MHC, IgSF and MhcSF.", Nucleic Acids Research, 38(suppl 1): D301-D307.
Ekiert et al., (2009), "Antibody Recognition of a Highly Conserved Influenza Virus Epitope.", Science, 324(5924): 246-251.
Garten et al. (2009), "Antigenic and Genetic Characteristics of Swine-Origin 2009 A(H1N1) Influenza Viruses Circulating in Humans.", Science, 325(5937): 197-201.
Gerhard et al., (1997), "Role of the B-cell response in recovery of mice from primary influenza virus infection.", Immunological Reviews, 159(1): 95-103.
Hancock et al., (2009), "Cross-Reactive Antibody Responses to the 2009 Pandemic H1N1 Influenza Virus.", New England Journal of Medicine, 361(20): 1945-1952.
Koelsch et al., (2007), "Mature B cells class switched to IgD are autoreactive in healthy individuals.", The Journal of Clinical Investigation, 117(6): 1558-1565.
Krause et al., (2010), "Naturally Occurring Human Monoclonal Antibodies Neutralize both 1918 and 2009 Pandemic Influenza A (H1N1) Viruses.", Journal of Virology, 84(6): 3127-3130.
Lefranc et al., (2009), "IMGT®, the international ImMunoGeneTics information system®.", Nucleic Acids Research, 37(suppl 1): D1006-D1012.
Luke et al., (2006), "Meta-Analysis: Convalescent Blood Products for Spanish Influenza Pneumonia: A Future H5N1 Treatment?", Annals of Internal Medicine, 145(8): 599-609.
Manicassamy et al., (2010), "Protection of Mice against Lethal Challenge with 2009 H1N1 Influenza A Virus by 1918-Like and Classical Swine H1N1 Based Vaccines.", PLoS Pathog, 6(1): e1000745.
McKean et al., (1984), "Generation of antibody diversity in the immune response of BALB/c mice to influenza virus hemagglutinin.", Proceedings of the National Academy of Sciences, 81(10): 3180-3184.

(Continued)

*Primary Examiner* — Agnieszka Boesen
(74) *Attorney, Agent, or Firm* — Emory Patent Group

(57) ABSTRACT

Antibodies or antibody fragments, wherein the antibody or the fragment binds HA domain of influenza virus (e.g. H1N1, H5N1, or both). Also described are cloned human antibodies that bind influenza.

5 Claims, 15 Drawing Sheets

(56) References Cited

PUBLICATIONS

Figure 1A:
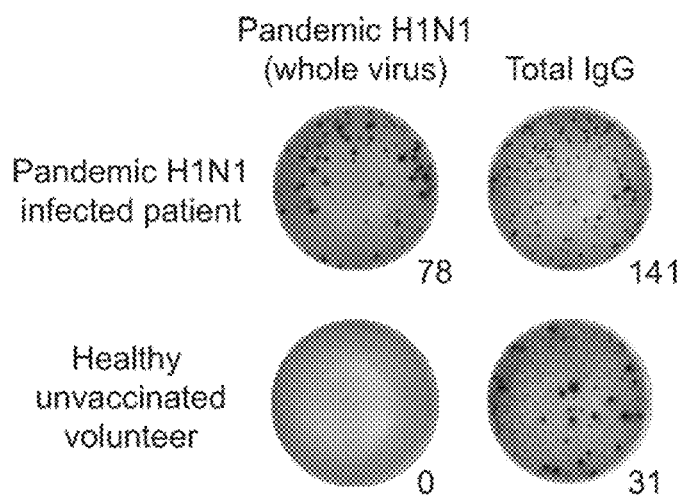

Okuno et al., (1993), "A common neutralizing epitope conserved between the hemagglutinins of influenza A virus H1 and H2 strains.", Journal of Virology, 67(5): 2552-2558.

Palladino et al., (1995), "Virus-neutralizing antibodies of immunoglobulin G (IgG) but not of IgM or IgA isotypes can cure influenza virus pneumonia in SCID mice.", Journal of Virology, 69(4): 2075-2081.

Puck et al., (1980), "Protection of Infants from Infection with Influenza A Virus by Transplacentally Acquired Antibody.", Journal of Infectious Diseases, 142(6): 844-849.

Renegar et al., (2004), "Role of IgA versus IgG in the Control of Influenza Viral Infection in the Murine Respiratory Tract.", The Journal of Immunology, 173(3): 1978-1986.

Reuman et al., (1983), "Maternal-infant transfer of influenza-specific immunity in the mouse.", The Journal of Immunology, 130(2): 932-936.

Sasaki et al., (2007), "Comparison of the Influenza Virus-Specific Effector and Memory B-Cell Responses to Immunization of Children and Adults with Live Attenuated or Inactivated Influenza Virus Vaccines.", Journal of Virology, 81(1): 215-228.

Simmons et al., (2007), "Prophylactic and Therapeutic Efficacy of Human Monoclonal Antibodies against H5N1 Influenza.", PLoS Med, 4(5): e178.

Smith et al., (2009), "Rapid generation of fully human monoclonal antibodies specific to a vaccinating antigen.", Nat. Protocols, 4(3): 372-384.

Steel et al., (2010), "Influenza Virus Vaccine Based on the Conserved Hemagglutinin Stalk Domain.", mBio, 1(1).

Subbarao et al., (2007), "Scientific barriers to developing vaccines against avian influenza viruses.", Nat Rev Immunol, 7(4): 267-278.

Sui et al., (2004), "Potent neutralization of severe acute respiratory syndrome (SARS) coronavirus by a human mAb to S1 protein that blocks receptor association.", Proceedings of the National Academy of Sciences of the United States of America, 101(8): 2536-2541.

Sui et al., (2009), "Structural and functional bases for broad-spectrum neutralization of avian and human influenza A viruses.", Nat Struct Mol Biol, 16(3): 265-273.

Sweet et al., (1987), "Production of passive immunity in neonatal ferrets following maternal vaccination with killed influenza A virus vaccines.", Immunology, 60(1): 83-89.

Wang et al., (2010), "Broadly Protective Monoclonal Antibodies against H3 Influenza Viruses following Sequential Immunization with Different Hemagglutinins.", PLoS Pathog, 6(2): e1000796.

Wardemann et al., (2003), "Predominant Autoantibody Production by Early Human B Cell Precursors.", Science, 301(5638): 1374-1377.

Wei et al., (2010), "Induction of Broadly Neutralizing H1N1 Influenza Antibodies by Vaccination.", Science, 329(5995): 1060-1064.

Wrammert et al. (2008). "Rapid cloning of high-affinity human monoclonal antibodies against influenza virus." Nature 453(7195): 667-671.

Xu et al., (2010), "Structural Basis of Preexisting Immunity to the 2009 H1N1 Pandemic Influenza Virus.", Science, 328 (5976): 357-360.

Zheng et al., (2004), "Human immunoglobulin selection associated with class switch and possible tolerogenic origins for Cδ class-switched B cells.", The Journal of Clinical Investigation, 113(8): 1188-1201.

Zheng et al., (2005), "Intricate targeting of immunoglobulin somatic hypermutation maximizes the efficiency of affinity maturation.", The Journal of Experimental Medicine, 201(9): 1467-1478.

Supplemental information from WRAMMERT et al., 2008, "Rapid cloning of high-affinity human monoclonal antibodies against influenza virus", Nature, 453(7915):667-671.

Wilson, Gene Bank Accession No. FJ475055, Cloning vector AbVec-hIgG1, Antibody variable gene expression vector for human IgG1 heavy chain, 2008.

Wrammert, J, et al., 2011, Broadly cross-reactive antibodies dominate the human B cell response against 2009 pandemic H1N1 influenza virus infection, The Journal of Experimental Medicine, 208(1): 181-193.

Brusco et al. "Variability of the immunoglobulin heavy chain constant region locus: a population study" Hum Genet, 1995; 95: 319-326.

Fett et al. "The Variability of Human 2-Chain Constant Regions and Some Relationships to V-Region Sequences" Immunochemistry, 1976; 13: 149-155.

Jefferis et al. "Human immunoglobulin allotypes" mAbs, 2009; 1(4): 1-7.

* cited by examiner

TABLE 2

| | A | B | C | D | E | F | G | H |
|---|---|---|---|---|---|---|---|---|
| 1 | Name | Functionality | V-GENE and allele | J-GENE and allele | D-GENE and allele | V-D-J-REGION | V-J-REGION | V-REGION |
| 68 | 70-5B03H-1 | productive | IGHV1-69*01 | IGHJ4*02 | IGHD1-26*01 | QVQLVQSGAEVKKPGSSVKVSCK ASGGTFRNFAVSWVRQAPGQGP EWMGGIIAIFGTAKYAQKFQGRVTI SADESTRIVQMELSSLRSDDTAIY YCASSSGSYYGDYFDYWGQGTL VTVSS SEQ ID NO: 22 | | QVQLVQSGAEVKKPGSSVKVSCKAS GGTFRNFAVSWVRQAPGQGPEWM GGIIAIFGTAKYAQKFQGRVTISADES TRIVQMELSSLRSDDTAIYYCA SEQ ID NO: 24 |
| 69 | 70-5B03K1 | productive | IGKV3-15*01 | IGKJ1*01 | | | EIVMTQSPATLSVSP GERATLSCRASQSV SSNLAWYQQTPGQ APRLLIYAASSRATGI PARFSGSGSGTEFT LSISSLQPEDFAVY CQQYNNWPRTFGQ GTKVEIK SEQ ID NO: 23 | EIVMTQSPATLSVSPGERATLSCRAS QSVSSNLAWYQQTPGQAPRLLIYAA SSRATGIPARFSGSGSGTEFTLSISSL QPEDFAVYCQQYNNWP SEQ ID NO: 25 |

| | A | I | J | K | L | M | N | O | P | Q |
|---|---|---|---|---|---|---|---|---|---|---|
| 1 | Name | FR1-IMGT | CDR1-IMGT | FR2-IMGT | CDR2-IMGT | FR3-IMGT | CDR3-IMGT | JUNCTION | J-REGION | FR4-IMGT |
| 68 | 70-5B03H-1 | QVQLVQSGAE VKKPGSSVKVS CKAS SEQ ID NO: 26 | GGTFRNFA SEQ ID NO: 28 | VSWVRQAPGQ GPEWMGG SEQ ID NO: 30 | IIAIFGTA SEQ ID NO: 32 | KYAQKFQGRVT ISADESTRIVQM ELSSLRSDDTAI YYC SEQ ID NO: 34 | ASSSGSYYGDY FDY SEQ ID NO: 36 | CASSSGSYYG DYFDYW SEQ ID NO: 38 | YFDYWGQGTL VTVSS SEQ ID NO: 40 | WGQGTLVTVS S SEQ ID NO: 42 |
| 69 | 70-5B03K1 | EIVMTQSPATLS VSPGERATLSC RAS SEQ ID NO: 27 | QSVSSN SEQ ID NO: 29 | LAWYQQTPGQ APRLLIY SEQ ID NO: 31 | AAS SEQ ID NO: 33 | SRATGIPARFS GSGSGTEFTLS ISSLQPEDFAVY YC SEQ ID NO: 35 | QQYNNWPRT SEQ ID NO: 37 | CQQYNNWPRT F SEQ ID NO: 39 | TFGQGTKVEIK SEQ ID NO: 41 | FGQGTKVEIK SEQ ID NO: 43 |

FIG. 11

ANTIBODIES DIRECTED AGAINST INFLUENZA

CROSS REFERENCE TO RELATED APPLICATIONS

This application is the National Stage of International Application No. PCT/US2012/020824 filed Jan. 10, 2012, which claims the benefit of priority to U.S. Provisional Application No. 61/431,406 filed Jan. 10, 2011, which applications are hereby incorporated by this reference in their entireties.

GOVERNMENT SUPPORT

This invention was made with government support under Grants U19-A1057266, U19 AI057266-0652, RR025008, HHSN266200700006C and 5U19A1062629-05 awarded by the National Institutes of Health. The Government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 11049_2016-08-18_ST25.txt. The text file is 16 KB, was created on Aug. 18, 2016, and is being submitted electronically via EFS-Web.

BACKGROUND

Influenza is the seventh leading cause of death in the United States (Beigel, 2008). The elderly, the very young, pregnant women and otherwise immune-compromised populations account for over 90% of influenza-related deaths. The pandemic H1N1 influenza virus strain is immunologically distinct from other influenza viruses, leaving large population groups susceptible to infection (Brockwell-Staats et al., 2009; Dawood et al., 2009; Garten et al., 2009; Hancock et al., 2009). The CDC reports that the 2009 H1N1 pandemic strain caused an estimated 60 million cases and 256,000 hospitalizations. An unusually high frequency of severe disease occurred in younger and otherwise healthy patients (Hancock et al., 2009). In addition, rare infections with avian H5N1 influenza strains in humans had close to a 50% mortality rate (Subbarao and Joseph, 2007). Emergence of a zoonotic or antigenically distinct strain that combined even a fraction of the morbidity and mortality of the pandemic H1N1 and H5N1 viruses would have dire consequences. Antibodies play a key role in protection against influenza infection in vivo (Gerhard et al., 1997; Luke et al., 2006; Puck et al., 1980; Simmons et al., 2007). The fact that there was little or no pre-existing antibody titers present prior to the emergence of this pandemic virus, and that the virus atypically caused such severe disease in young adults illustrates the importance of comprehensively understanding the B cell responses and antibody specificities induced by infection with this influenza virus.

SUMMARY OF THE INVENTION

Described herein are antibodies, antibody fragments and peptides wherein the antibody or the antibody fragment or the peptide binds to an HA domain of influenza (e.g., H1N1, H5N1 or both) virus and comprises: (a) a VH CDR1 comprising or consisting of an amino acid sequence identical to or having 1, 2, or 3 amino acid residue substitutions or deletions relative to a VH CDR1 in column J of Table 2; (b) a VH CDR2 comprising or consisting of an amino acid sequence identical to or having 1, 2, or 3 amino acid residue substitutions or deletions relative to a VH CDR2 in column L of Table 2; (c) a VH CDR3 comprising or consisting of an amino acid sequence identical to or having 1, 2, or 3 amino acid residue substitutions or deletions relative to a VH CDR3 in column N of Table 2; (d) a VL CDR1 comprising or consisting of an amino acid sequence identical to or having 1, 2, or 3 amino acid residue substitutions or deletions relative to a VL CDR1 in column J of Table 2; (e) a VL CDR2 comprising or consisting of an amino acid sequence identical to or having 1, 2, or 3 amino acid residue substitutions or deletions relative to a VL CDR2 in column L of Table 2; and (f) a VL CDR3 comprising or consisting of an amino acid sequence identical to or having 1, 2, or 3 amino acid residue substitutions or deletions relative to a VL CDR3 in column N of Table 2.

In some cases the antibody, antibody fragment or peptide binds to the HA domain of H1N1 influenza. In some cases it binds the HA of H5N1 influenza. In some cases it binds the HA of both H1N1 and H5N1. Thus, the antibody, antibody fragment or peptide binds to the HA domain of two or more different subclasses of influenza A. The antibody, antibody fragment or peptide can cross-react with two different influenza strains (e.g., two or more different strains of H1N1 such as the 2009 pandemic strain or the 1918 pandemic strain). In some cases, the antibody, antibody fragment or peptide may cross-react with three or more, five or more or ten or more different influenza strains. Thus, the antibody, antibody fragment or peptide binds to the HA domain (and in some cases can neutralize) two or more of the following H1N1 strains: A/Brisb/59/07, A/BrMis/1/1918, A/Indo/5/05, A/NewCal/20/99 and a/SolIs/3/06. Some antibodies, antibody fragments and peptides immunospecifically bind to a particular type of influenza, e.g., H1N1 or H5N1. In some cases the antibody, antibody fragment or peptide immunospecifically binds to an influenza, e.g., influenza A, HA domain.

Also described are purified antibodies, antibody fragments and peptides that bind to an HA domain of (e.g., H1N1, H5N1 or both) influenza virus and comprises: (a) a VH CDR1 comprising or consisting of the amino acid sequence of a VH CDR1 in column J of Table 2; (b) a VH CDR2 comprising or consisting of the amino acid sequence of a VH CDR2 in column L of Table 2; (c) a VH CDR3 comprising or consisting of the amino acid sequence of a VH CDR3 in column N of Table 2; (d) a VL CDR1 comprising or consisting of the amino acid sequence of VL CDR1 in column J of Table 2; (e) a VL CDR2 comprising or consisting of the amino acid sequence of a VL CDR2 in column L of Table 2; and (f) a VL CDR3 comprising or consisting of the amino acid sequence of a VL CDR3 in column N of Table 2.

Also described is an isolated antibody or antibody fragment, wherein the antibody or the fragment: (i) comprises a VH chain domain comprising three CDRs and a VL chain domain comprising three CDRs; and (ii) binds an HA domain of influenza virus (e.g., H1N1, H5N1 or both) wherein the three CDRs of the VH chain domain comprise: (a) a VH CDR1 comprising the amino acid sequence of a VH CDR1 in column J of Table 2; (b) a VH CDR2 comprising the amino acid sequence of a VH CDR2 in column L of Table 2; and (c) a VH CDR3 comprising the amino acid sequence of a VH CDR3 in column N of Table 2.

Also described is a purified antibody or antibody fragment, wherein the antibody or the fragment: (i) comprises a VH chain domain comprising three CDRs and a VL chain domain comprising three CDRs; and (ii) binds an HA domain of influenza virus (e.g., H1N1, H5N1 or both) wherein the three CDRs of the VL chain domain comprise: (a) a VL CDR1 comprising the amino acid sequence of VL CDR1 in column J of Table 2; (b) a VL CDR2 comprising the amino acid sequence of a VL CDR2 in column L of Table 2; and (c) a VL CDR3 comprising the amino acid sequence of a VL CDR3 in column N of Table 2.

Also described is a purified antibody or antibody fragment, wherein the antibody or the fragment binds the HA domain of an influenza virus (e.g., H1N1, H5N1 or both) and comprises a heavy chain variable domain having an amino acid sequence identical to or comprising up to 10 (e.g., up to 9, 8, 7, 6, 5, 4, 3, 2 or 1) amino acid residue substitutions relative to the amino acid sequence of the heavy chain variable domain (column H) of a selected antibody in Table 2 and comprises a light chain variable domain having an amino acid sequence identical to or comprising up to 10 (e.g., up to 9, 8, 7, 6, 5, 4, 3, 2 or 1) amino acid residue substitutions relative to the amino acid sequence of the light chain variable domain (column H) of the selected antibody in Table 2.

Also described is a purified antibody or antibody fragment, wherein the antibody or the fragment binds an HA domain of influenza virus (e.g., H1N1, H5N1 or both) and comprises a heavy chain variable domain having at least 90% or 95% identity to the amino acid sequence of the heavy chain variable domain (column H) of a selected antibody in Table 2 and comprises a light chain variable domain having at least 90% or 95% identity to the amino acid sequence of the light chain variable domain (column H) of the selected antibody in Table 2.

Also described is a purified antibody or antibody fragment, wherein the antibody or the fragment binds an HA domain of influenza virus (e.g., H1N1, H5N1 or both) and comprises a heavy chain variable domain having the amino acid sequence of the heavy chain variable domain sequence (column H) of a selected antibody in Table 2 and the light chain variable domain having the amino acid sequence of the light chain variable domain sequence (column H) of the selected antibody in Table 2.

Also described is a purified antibody or antibody fragment, wherein the antibody or the fragment binds the same epitope on an HA domain of influenza virus (e.g., H1N1, H5N1 or both) as that bound by an antibody comprising: (a) a heavy chain variable domain having the amino acid sequence of the heavy chain variable domain sequence (column H) of a selected antibody in Table 2; and (b) a light chain variable domain having the amino acid sequence of the light chain variable domain sequence (column H) of the selected antibody in Table 2.

Also described is a purified antibody or antibody fragment, wherein the antibody or the fragment binds to an HA domain of influenza virus (e.g., H1N1, H5N1 or both), comprising: (a) a polypeptide comprising an amino acid sequence identical to or having up to 5 amino acid substitutions compared to a V-D-J sequence in column F of Table 2; and (a) a polypeptide comprising an amino acid sequence identical to or having up to 5 amino acid substitutions compared to a V-J sequence in column G of Table 2.

Also described is a purified antibody or antibody fragment, wherein the antibody or the fragment binds to an HA domain of influenza virus (e.g., H1N1, H5N1 or both), comprising: (a) a polypeptide comprising an amino acid sequence identical to or having up to 5 amino acid substitutions compared to the V-D-J sequence in column F of Table 2 of a selected antibody; and (a) a polypeptide comprising an amino acid sequence identical to or having up to 5 amino acid substitutions compared to a V-J sequence in column G of Table 2 of the selected antibody.

In various embodiments the purified antibody binds the HA stalk; binds the HA globular head; neutralizes one or more strains H1N1 influenza, one or more strains of H5N1 influenza or one or more strains of both H1N1 and H5N1 influenza; has hemagglutination inhibition activity; does not have hemagglutination inhibition activity; binds to at least 3 H1 influenza strains selected from the strains in panel A of FIG. 8; binds to at least 5 H1 influenza strains selected from the strains in panel A of FIG. 8; is an IgG antibody; is an IgG1 antibody; is an IgG1, kappa antibody; is an IgG1, lambda antibody; is selected from an IgM, IgA, IgD and IgE antibody; is selected from a Fab, a F(ab')2 fragment, a Fd fragment, an Fv fragment, a scFv, and a dAb fragment; is a monoclonal antibody; is a humanized antibody or a fully human antibody.

In some cases the antibody, antibody fragment or peptide binds or binds and neutralizes H1N1 and H1H5.

In the case of an antibody, antibody fragment or peptide comprising a CDR1, CDR2 and CDR3 (VH or VL) having 1, 2, or 3 amino acid residue substitutions or deletions relative in Table 2 to a CDR1, CDR2 or CDR3 Table 2, in some cases the substitutions are conservative and in some cases deletions are contiguous and in some case are at the amino or carboxy terminus such that the CDR contains 2, 3, 4, 5, 6, 7, 8, 9, 10, 11, 12, 13, 14, 15, 16, 17, 18 or 19 contiguous amino acids of a CDR depicted in Table 2.

In certain cases the antibody, antibody fragment or peptide comprises the heavy chain and light chain CDRs of an antibody selected from: 1009-3D06, 1009-3B05, 70-1F02 and 70-3B03.

In some cases the antibody, antibody fragment or peptide comprises:

a) a CDR1 comprising at least 7 contiguous amino acids of GMTSNSLA (SEQ ID NO. 1); a CDR2 comprising at least 7 contiguous amino acids of IIPVFETP (SEQ ID NO 2); and a CDR3 comprising at least 14 or 15 contiguous amino acids of ATSAGGIVNYYLSFNI; (SEQ ID NO. 3)

b) a CDR1 comprising GMTSNSLA (SEQ ID NO. 1); a CDR2 comprising IIPVFETP (SEQ ID NO 2); and a CDR3 comprising ATSAGGIVNYYLSFNI (SEQ ID NO. 3)

c) a heavy chain variable domain comprising: a CDR1 comprising GMTSNSLA (SEQ ID NO. 1); a CDR2 IIPVFETP (SEQ ID NO. 2); and a CDR3 comprising ATSAGGIVNYYLSFNI (SEQ ID NO. 3);

1. d) a heavy chain variable domain comprising:

(SEQ ID NO. 4)
QVQLVQSGAEVKKPGSSVKVSCKASGMTSNSLAISWVRQAPGQGLEWMG

GIIPVFETPKYAQKFQGRVTITADKSTNTAYMDLISLKSEDTAMYYCA;

e) a CDR1 comprising at least 5 contiguous amino acids of QTITTW (SEQ ID NO. 5); a CDR2 comprising at least 2 contiguous amino acids of KTS; and a CDR3 comprising at least 8 contiguous amino acids of QQYSTYSGT (SEQ ID NO. 6);

f) a CDR1 comprising QTITTW (SEQ ID NO. 5); a CDR2 comprising KTS;
and a CDR3 comprising QQYSTYSGT (SEQ ID NO. 6);

g) a light chain variable domain comprising: a CDR1 comprising QTITTW (SEQ ID NO. 5); a CDR2 comprising KTS; and a CDR3 comprising QQYSTYSGT (SEQ ID NO. 6);

h) a light chain variable domain comprising:

(SEQ ID NO. 7)
DIQMTQSPSTLSASVGDRVTITCRASQTITTWLAWYQQKPGQAPKLLIH

KTSTLETGVPSRFSGSGSGTQFTLTITNLQPDDSATYYCQQYSTY

In some cases the antibody, antibody fragment or peptide comprises:

a) a CDR1 comprising at least 8 contiguous amino acids of GGTSNNYP (SEQ ID NO. 8); a CDR2 comprising at least 7 contiguous amino acids of SIPIFNTP (SEQ ID NO. 9); and a CDR3 comprising at least 14 or 15 contiguous amino acids of ATSAGGIVNYFLLFDI (SEQ ID NO. 10)

b) a CDR1 comprising GGTSNNYP (SEQ ID NO. 8); a CDR2 comprising SIPIFNTP (SEQ ID NO. 9); and a CDR3 comprising ATSAGGIVNYFLLFDI (SEQ ID NO. 10);

c) a heavy chain variable domain comprising: a CDR1 comprising GGTSNNYP (SEQ ID NO. 8); a CDR2 comprising SIPIFNTP (SEQ ID NO. 9); and a CDR3 comprising ATSAGGIVNYFLLFDI (SEQ ID NO. 10);

d) a heavy chain variable domain comprising:

(SEQ ID NO. 11)
QVQLVQSGAELKKPGSSVKVSCKTSGGTSNNYPISWVRQAPGQGLEWMG

GSIPIFNTPKYGKKFQGRVTITSDTSTSTAYMELSSLRSDDTAIYYCA;

e) a CDR1 comprising at least 5 contiguous amino acids of QSISDW (SEQ ID NO. 12); a CDR2 comprising at least 2 contiguous amino acids of KAS; and a CDR3 comprising at least 8 contiguous amino acids of QHYNTYSGT (SEQ ID NO. 13);

f) a CDR1 comprising QSISDW (SEQ ID NO. 12); a CDR2 comprising KAS; and a CDR3 comprising QHYNTYSGT (SEQ ID NO. 13);

g) a light chain variable domain comprising: a CDR1 comprising QSISDW; a CDR2 comprising KAS; and a CDR3 comprising QHYNTYSGT (SEQ ID NO. 13);

h) a light chain variable domain comprising:

(SEQ ID NO. 14)
DIQMTQSPSTLSASVGDRVTIACRASQSISDWLAWYQQKPGKAPKLLIH

KASSLESGVPSRFSGGGSGTEFTLTISSLQADDSATYYCQHYNTY.

In some cases the antibody, antibody fragment or peptide comprises:

a) a CDR1 comprising at least 8 contiguous amino acids of GGIFRSNA (SEQ ID NO. 15); a CDR2 comprising at least 7 contiguous amino acids of IIAVFGTA (SEQ ID NO. 16); and a CDR3 comprising at least 14 or 15 contiguous amino acids of ARGPYYYGNSHLDF (SEQ ID NO. 17)

b) a CDR1 comprising GGIFRSNA (SEQ ID NO. 15); a CDR2 comprising IIAVFGTA (SEQ ID NO. 16); and a CDR3 comprising ARGPYYYGNSHLDF (SEQ ID NO. 17);

c) a heavy chain variable domain comprising: a CDR1 comprising GGIFRSNA (SEQ ID NO. 15); a CDR2 comprising IIAVFGTA (SEQ ID NO. 16); and a CDR3 comprising ARGPYYYGNSHLDF (SEQ ID NO. 17);

d) a heavy chain variable domain comprising:

(SEQ ID NO. 18)
QVQLVQSGAEVKKPGSSVKVSCRASGGIFRSNAISWVRQAPGQGLEWMG

EIIAVFGTANYAQKFQGRVTITADESTSTAYMELSSLRSEDTAVYYCA;

e) a CDR1 comprising at least 5 contiguous amino acids of QSVSSNY (SEQ ID NO. 19); a CDR2 comprising at least 2 contiguous amino acids of GAS; and a CDR3 comprising at least 8 contiguous amino acids of QQYGTSPRT (SEQ ID NO.20);

f) a CDR1 comprising QSVSSNY (SEQ ID NO. 19); a CDR2 comprising FAS; and a CDR3 comprising QQYGTSPRT (SEQ ID NO. 20);

g) a light chain variable domain comprising: a CDR1 comprising QSVSSNY (SEQ ID NO. 19); a CDR2 comprising GAS; and a CDR3 comprising QQYGTSPRT (SEQ ID NO. 20);

h) a light chain variable domain comprising:

(SEQ ID NO. 21)
EIVLTQSPGTLSLSPGERATLSCRASQSVSSNYLAWYQQKPGQAPRLLI

YGASNRATGIPDRFSGSGSGTDFTLAISRLEPEDFAVYYCQQYGTSP.

Also described is a sterile composition comprising the purified antibody or antibody fragment and a sterile composition comprising the purified antibody or antibody fragment and a pharmaceutically acceptable carrier.

Also described is an isolated nucleic acid encoding the antibody or antibody fragment; a vector comprising the nucleic acid; a host cell comprising the vector or nucleic acid.

Also descried are method for reducing the risk of infection with H1N1 and/or H5N1 influenza virus in a human subject, the method comprising administering the antibody or antibody fragment; a method for treating a human subject infected with H1N1 and/or H5N1 influenza virus, the method comprising administering the antibody or antibody fragment; a method of preventing H1N1 and/or H5N1 influenza disease in a human subject, said method comprising administering the antibody or antibody fragment; and a method of ameliorating one or more symptoms associated with an H1N1 and/or H1N1 influenza infection in a human subject, the method comprising administering the antibody or antibody fragment.

Also described is an antibody that binds the same epitope of HA as does: 1009-3D06, 1009-3B05, 70-1F02 and 70-3B03. Also described is a peptide that comprises the HA epitope bound by at least one of the following antibodies: 1009-3D06, 1009-3B05, 70-1F02 and 70-3B03. Also described is a pharmaceutical composition (e.g., a composition capable of eliciting an immune response to H1N1) comprising: 1) a peptide that comprises the HA epitope bound by at least one of the following antibodies: 1009-3D06, 1009-3B05, 70-1F02 and 70-3B03; 2) an adjuvant suitable for administering to a human patient. Also described is a method for eliciting an immune response in a patient by administering a peptide that comprises the HA epitope bound by at least one of the following antibodies: 1009-3D06, 1009-3B05, 70-1F02 and 70-3B03; and an optional adjuvant suitable for administering to a human.

DESCRIPTION OF THE FIGURES

FIG. 1A is a representative ELISPOT. Numbers of plasmablasts secreting antibody reactive to pandemic H1N1 is compared to the total number of IgG-secreting cells from each PBMC sample (numerals). All ELISPOT assays were performed in duplicate.

Figure 1B:
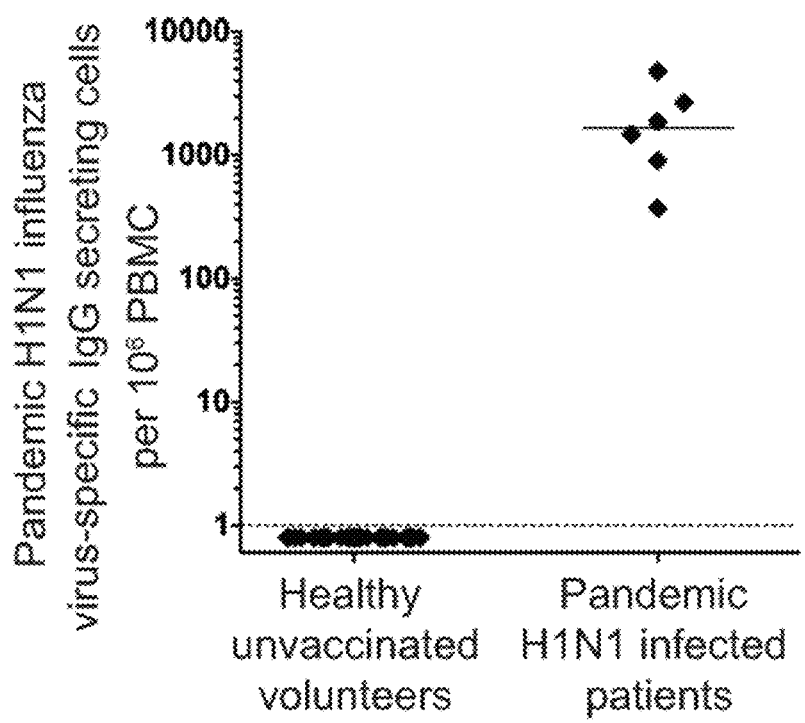

FIG. 1B is a summary of all the donors analyzed; each dot represents one patient or control. FIG. 1B shows Magnitude of the plasmablast response observed in peripheral blood of 6 pandemic H1N1 infected patients and 22 healthy (non-infected/non-vaccinated) donors by ELISPOT analysis.

Figure 1C:
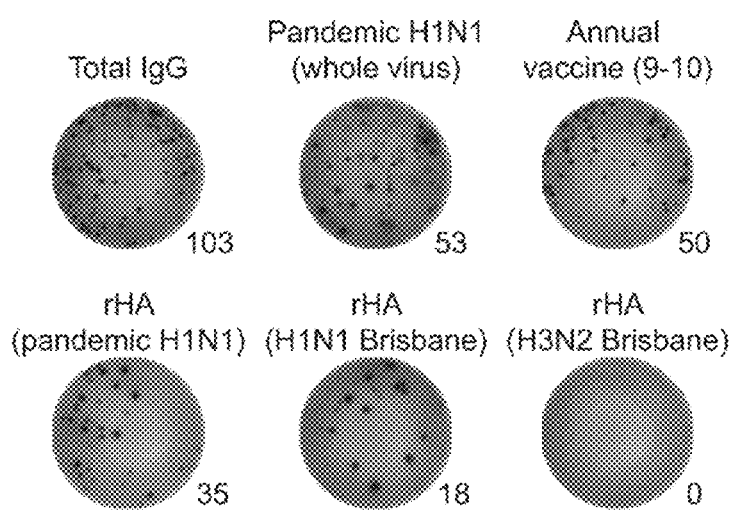

FIG. 1C shows they specificity of the sorted plasmablasts measured by ELISPOT analysis. Representative ELISPOT showing plasmablasts producing antibodies reactive with total IgG or pandemic H1N1 whole virus, annual influenza vaccine (2009/2010 TIV vaccine), or recombinant HA from pandemic H1N1, the previous year's annual vaccine H1N1 strain (A/Brisbane/59/2007), or the previous year's H3N2 strain (A/Brisbane/10/2007).

Figure 1D:
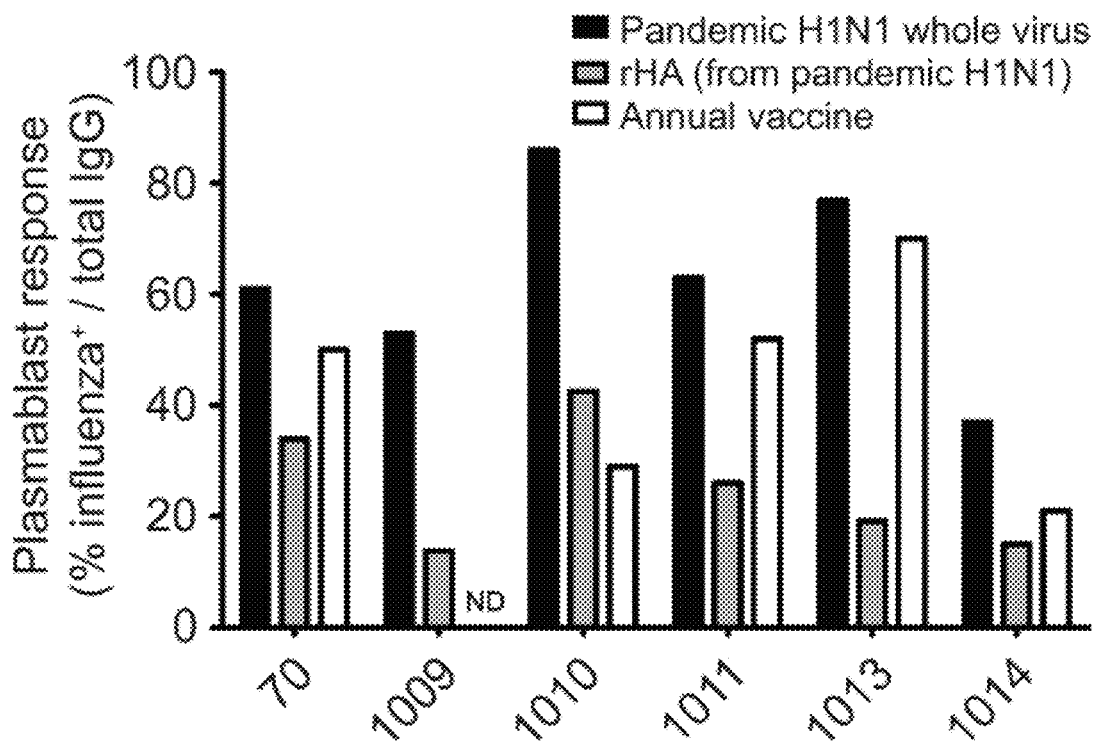

FIG. 1D is a summary of the frequency of whole IgG secreting cells specific pandemic H1N1 whole virus, recombinant HA from pandemic H1N1 and recombinant HA from the previous year's vaccine. Donors EM1 and SF1000 were not analyzed in this fashion as the antigens were not available for live-cell analyses at that time early in the pandemic.

Figure 1E:
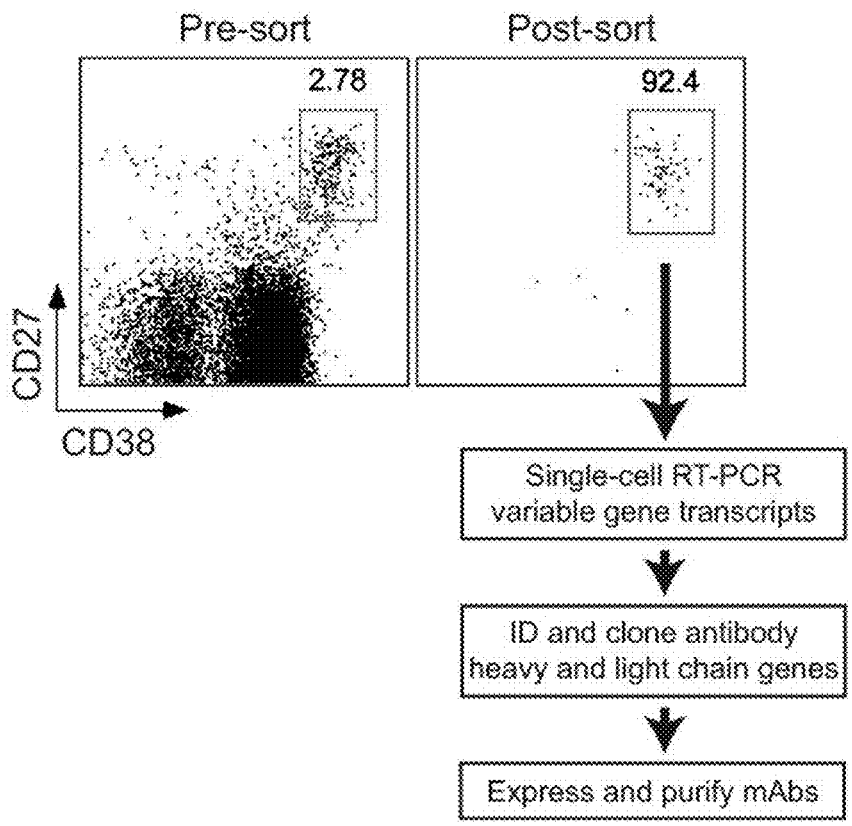

FIG. 1E shows the sorting of plasmablast cells from pandemic H1N1 influenza infected patients to generate mAbs. Flow cytometry plots show percentage of $CD27^{hi}CD38^{hi}$ cells (dot plots are gated on $CD3^-CD20^{lo/-}$ lymphocytes). The plasmablasts are defined herein as $CD3^-CD20^{lo/-}CD19^+CD38^{hi}CD27^{hi}$ cells. The right panel shows an example of post-sort purity of ungated cells (verified for each sample). Single plasmablasts were isolated from the sorted fraction by cell sorting, and variable antibody genes were cloned from individual cells.

Figure 1F:
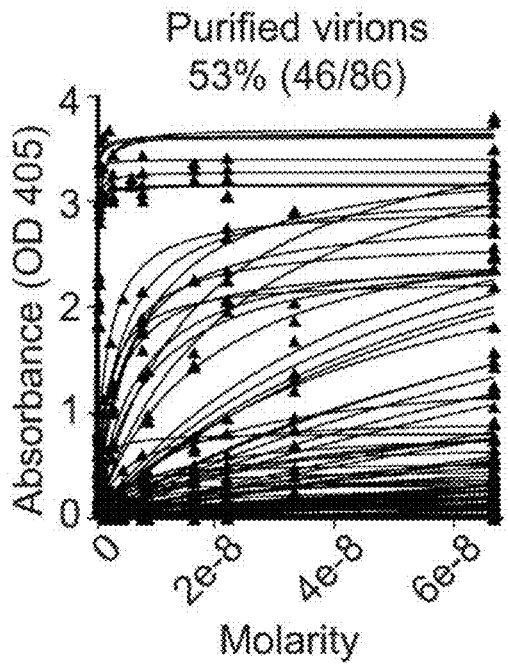

FIG. 1F is scatchardplots of binding of the isolated mAbs to pandemic H1N1 whole purified virus.

Figure 1G:
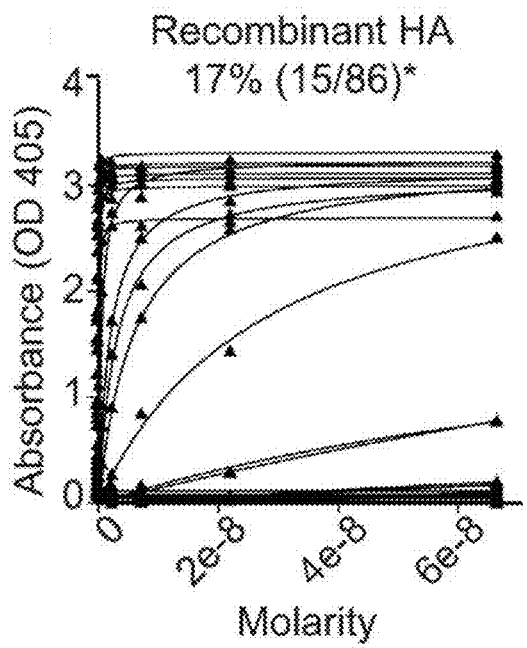

FIG. 1G is scatchardplots of binding of the isolated mAbs to pandemic H1N1 recombinant HA as measured by ELISA. Antibodies were scored positive (frequency above plots) if they bound at least 2 standard deviations greater than the mean absorbance of naive B cell antibodies at 10 ug/ml (detailed in FIG. 7A). Antibodies were tested at 10 ug/ml and 3-fold serial dilutions until a non-binding concentration was determined. Each antibody was tested in at least two (and typically more) replicates for specificity and affinity estimations. *Note that only 14 of 15 HA-binding antibodies have curves in FIG. 1G, because one of the HA-reactive antibodies only binds HA on whole virions, not on the recombinant protein.

Figure 2A:
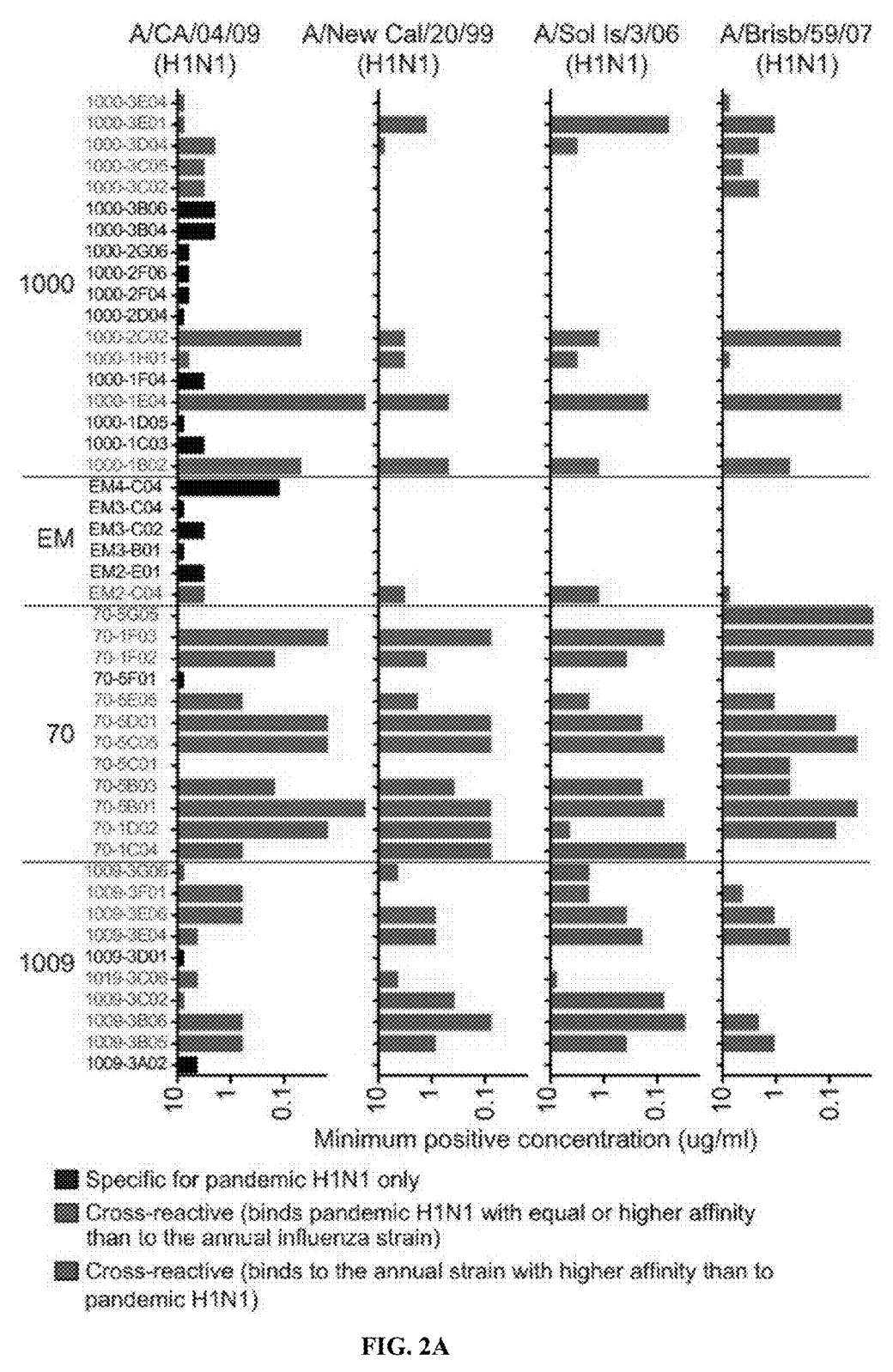
Figure 7A:
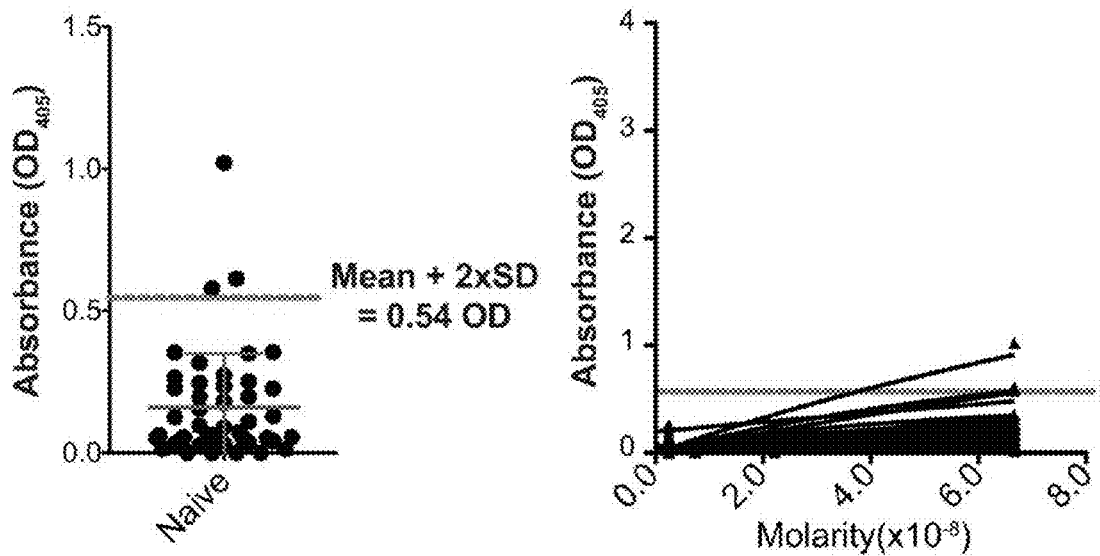

FIG. 2A shows Pandemic H1N1 reactive mAbs isolated from infected patients (1000, EM, 70, 1009) were assayed for binding to annual H1N1 influenza strain whole virus. The minimum detectable concentration is defined as two standard deviations above the mean binding of 48 randomly chosen naïve B cell antibodies (FIG. 7A). Bars are color coded to approximate levels of cross-reactivity to the annual vaccine (circulating) strains of recent years.

Figure 2B:
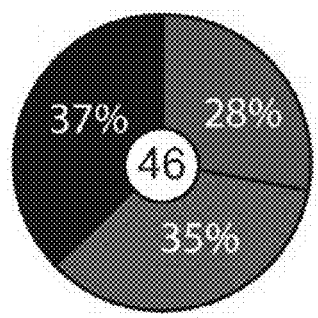

FIG. 2B use the same color scheme. Each value is representative of at least two replicate ELISAs repeated until a single consistent minimum concentration was established. Center numeral equals total antibodies.

Figure 2C:
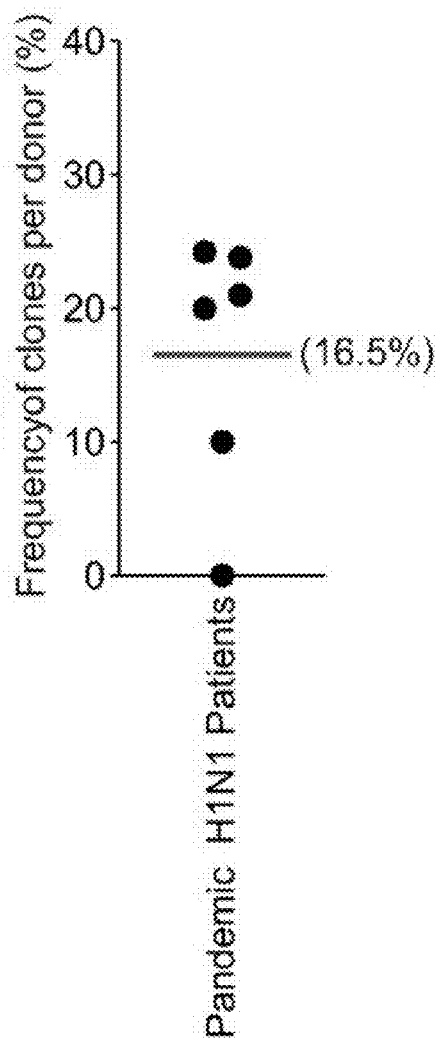

FIG. 2C is an analysis of the variable gene sequences from plasmablasts of the four pandemic H1N1 infected patients indicated that approximately 16.5% of the pandemic H1N1 induced plasmablasts were clonally-related (shared identical VH and JH genes and CDR3 junctions).

Figure 2D:
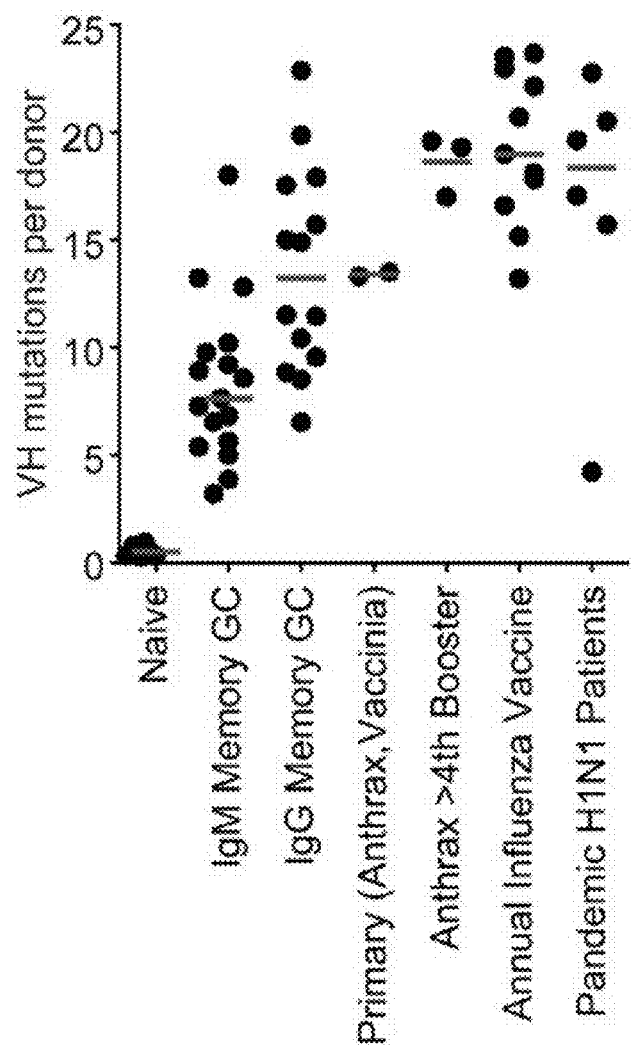

FIG. 2D shows the average number of somatic hypermutations in the pandemic H1N1 patient plasmablast variable region genes compared to primary IgG plasmablast responses to vaccinia (small pox) or the anthrax vaccine, or after at least 4 boosters with the anthrax vaccine. To account for the obvious outlier in the pandemic H1N1 group (patient-EM), median values are indicated by the bar. Students t-tests excluding the outlier indicated a p-value of <0.04 for the remaining five pandemic H1N1 samples compared to the IgG memory and GC cells or the primary IgG plasmablast responses (0.2 with EM included), and <0.0001 against the IgM populations. Notably, besides patient-EM, each individual set of VH genes averaged significantly more mutations than the IgG memory and GC or the primary responses (FIG. 9A). Each point represents one individual donor and is averaged from 25 to 75 sequences except for the primary response to anthrax from which only 10 VH genes could be cloned from single cells do to the highly limited response. Mutations accumulated per individual sequence are depicted in FIG. 9.

Figure 3A:
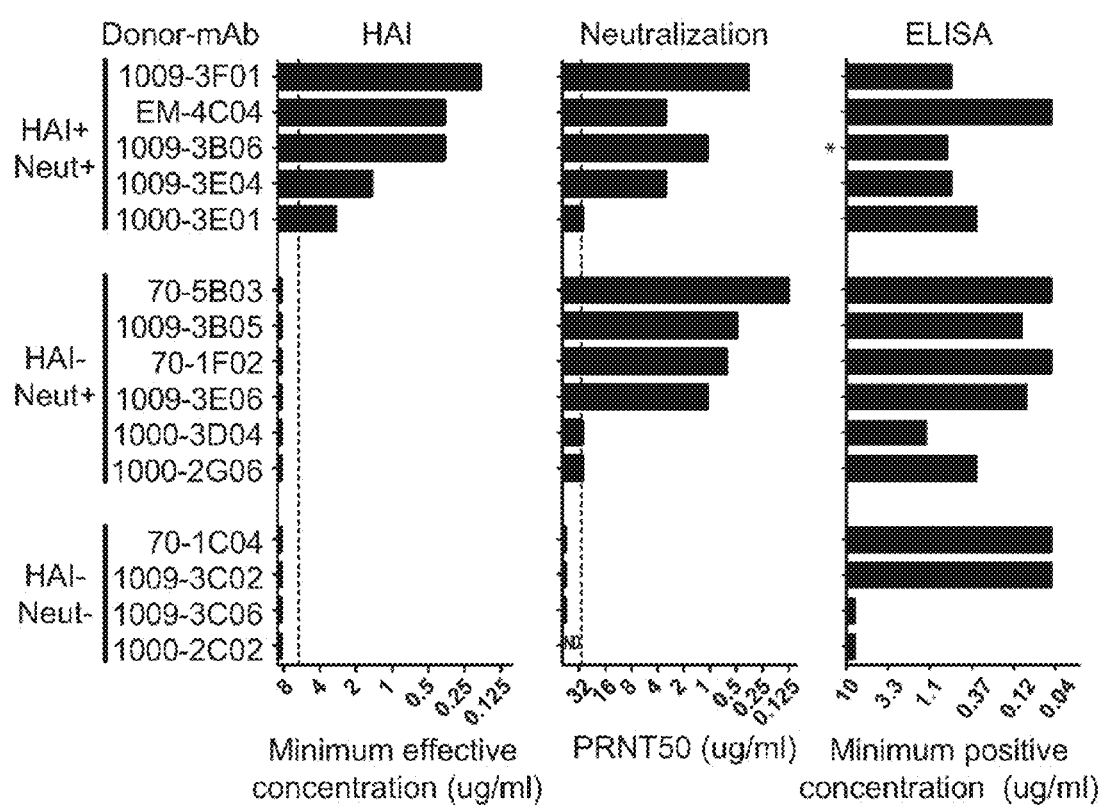

FIG. 3A shows In vitro functional analysis of 15 antibodies from indicated patients that bound pandemic H1N1 influenza recombinant HA protein. The left panel shows HAI (HA-inhibition) minimum effective antibody concentration, the middle panel shows PRNT50 plaque reduction neutralization minimum effective antibody concentration, and the right panel shows ELISA binding summarized as minimum positive concentration (defined for FIG. 2) against recombinant HA (original curves are in FIG. 1F and FIG. 8A). The antibodies are grouped based on whether they show HAI and/or neutralizing (neut) function. Antibody 1009-3B06 was only tested for binding to whole virus as this antibody did not bind to rHA due to binding of a quaternary or conformationally sensitive epitope that is not present in the recombinant protein. HAI and neutralization assays were performed in duplicate and repeated at least three times. ELISA curves are provided in FIG. 8A.

Figure 3B:
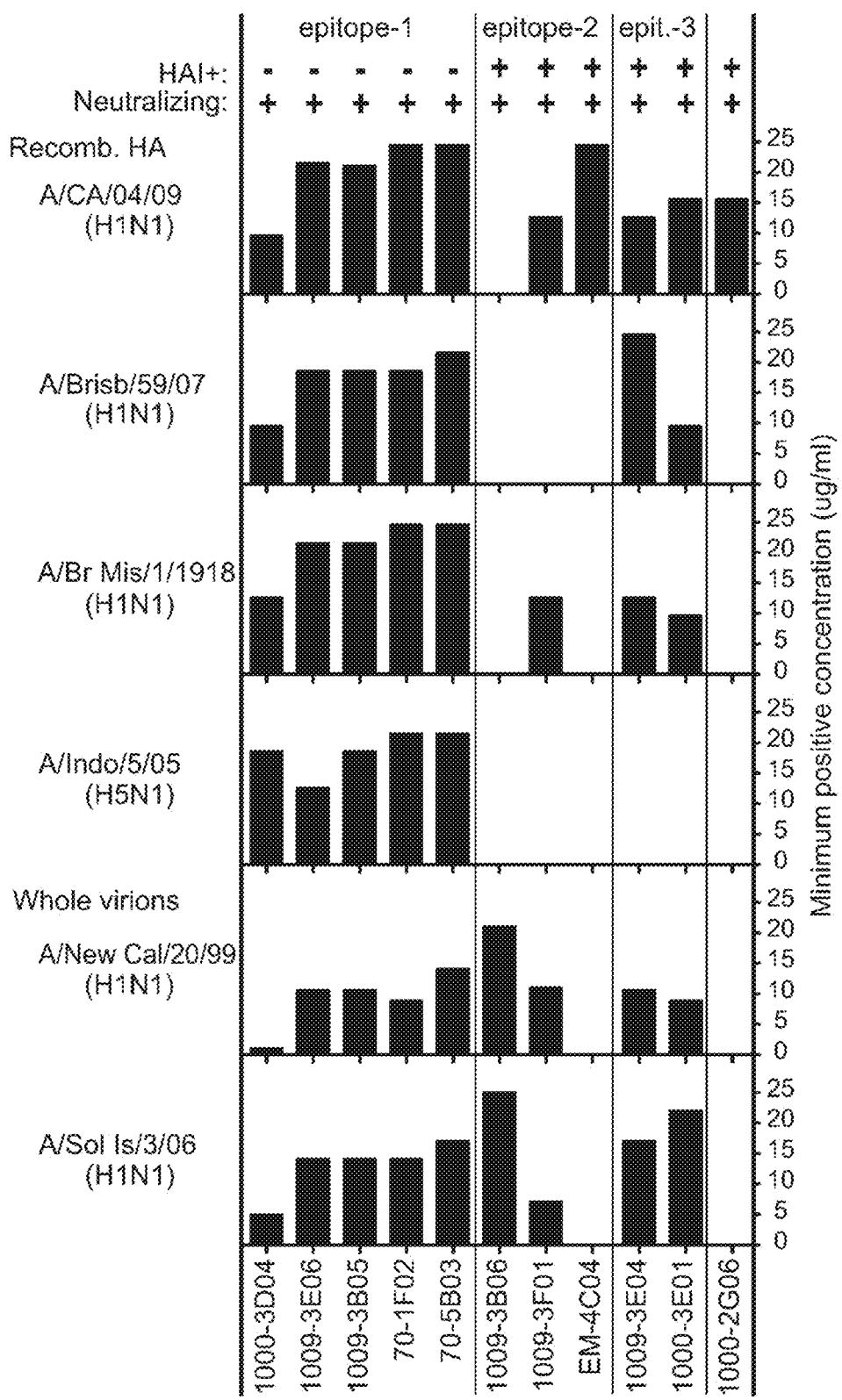
Figure 8A:
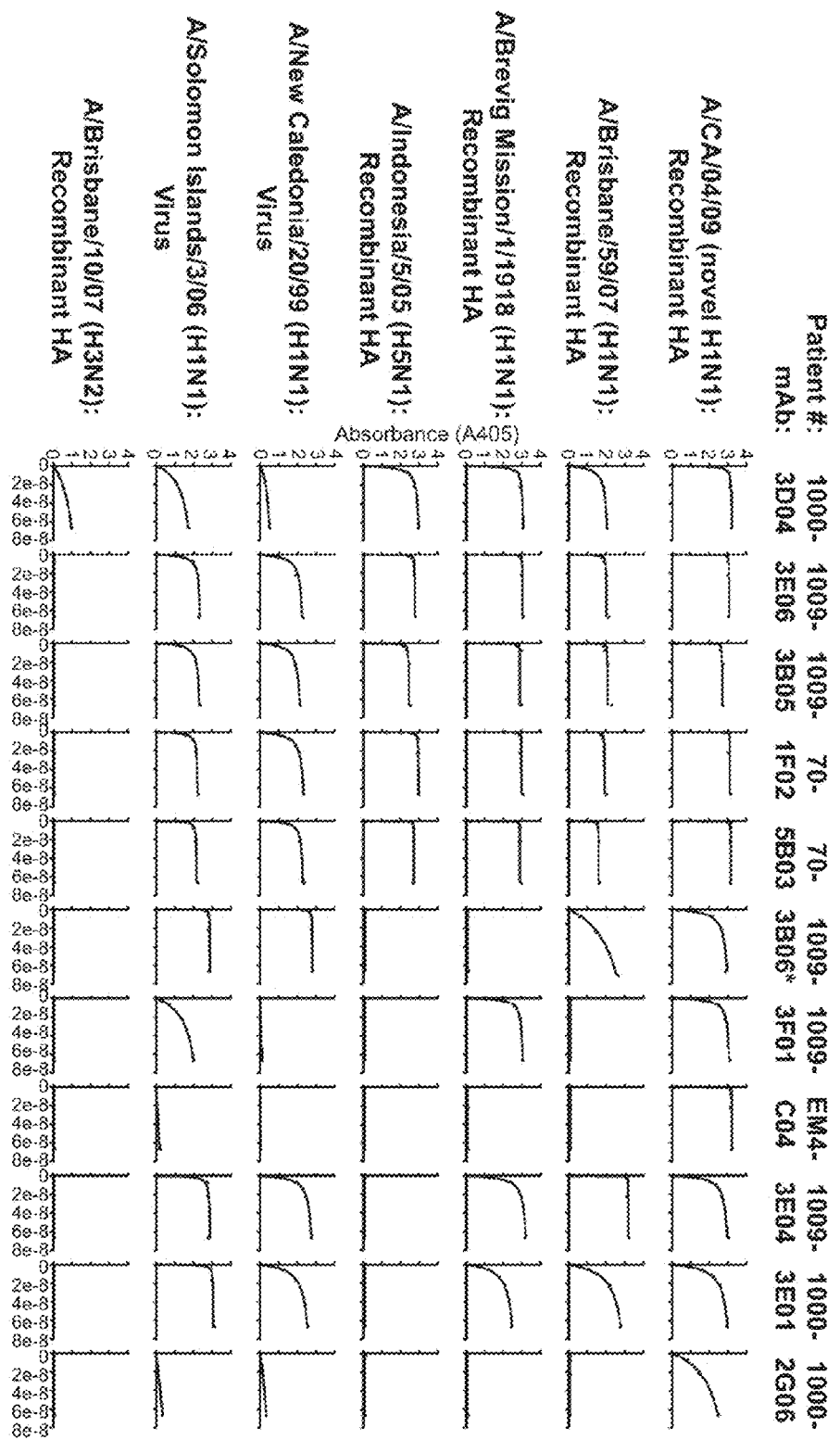
Figures 8B, 9A:
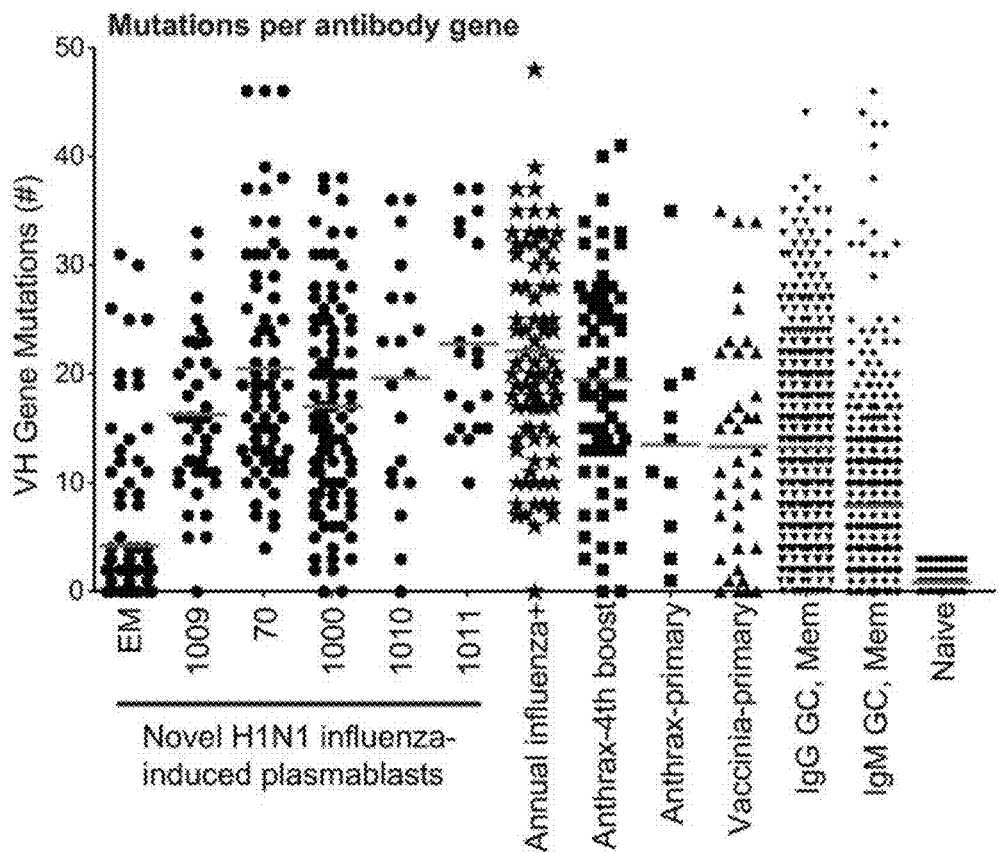

FIG. 3B shows ELISA binding as shown by minimum positive concentration (defined for FIG. 2) of neutralizing mAbs to rHA or whole virions from pandemic H1N1 or other influenza strains (ELISA binding curves are provided in FIG. 8A). Three binding patterns (epitopes 1 and 2, and 3) were observed that coincided with specificity comparisons by competitive ELISA as illustrated in FIG. 4A.

Figure 3C:
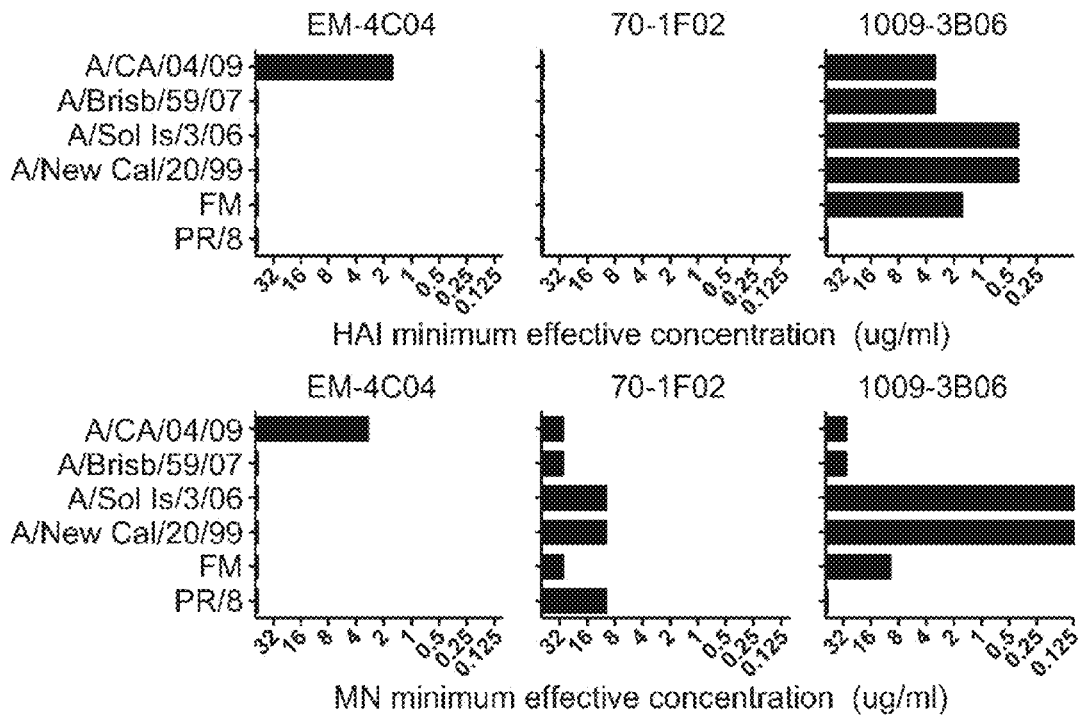

FIG. 3C is representative neutralizing antibodies (EM-4C04, 70-1F02, 1009-3B06) were used for HAI and microneutralization (MN) activity against pandemic H1N1 and several other annual or laboratory H1N1 influenza strains. Experiments were performed in duplicates and repeated at least three times. Minimum effective concentration is shown for both assays.

Figure 4A:
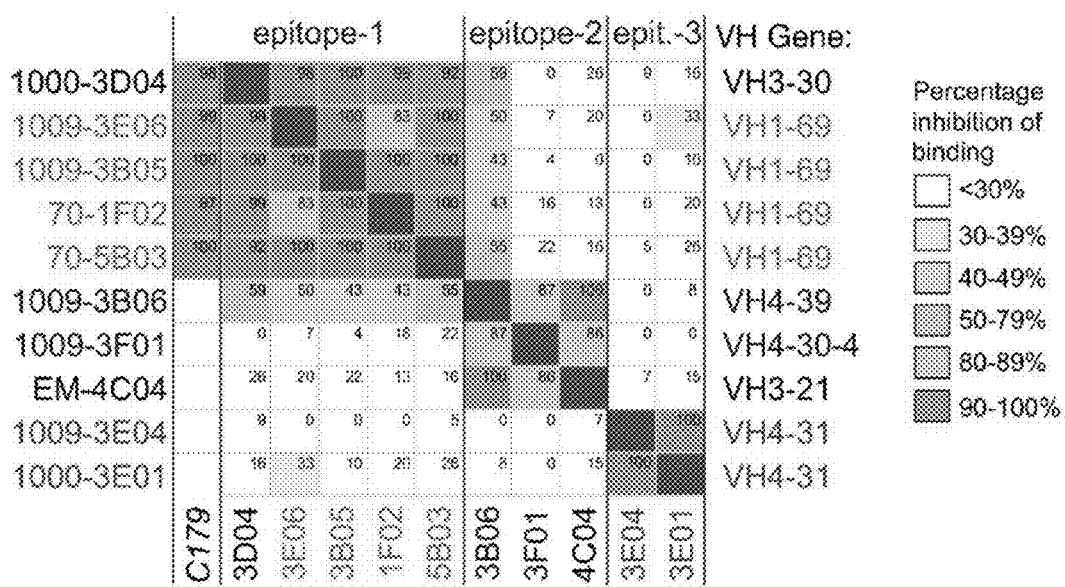
Figures 4B, 5:
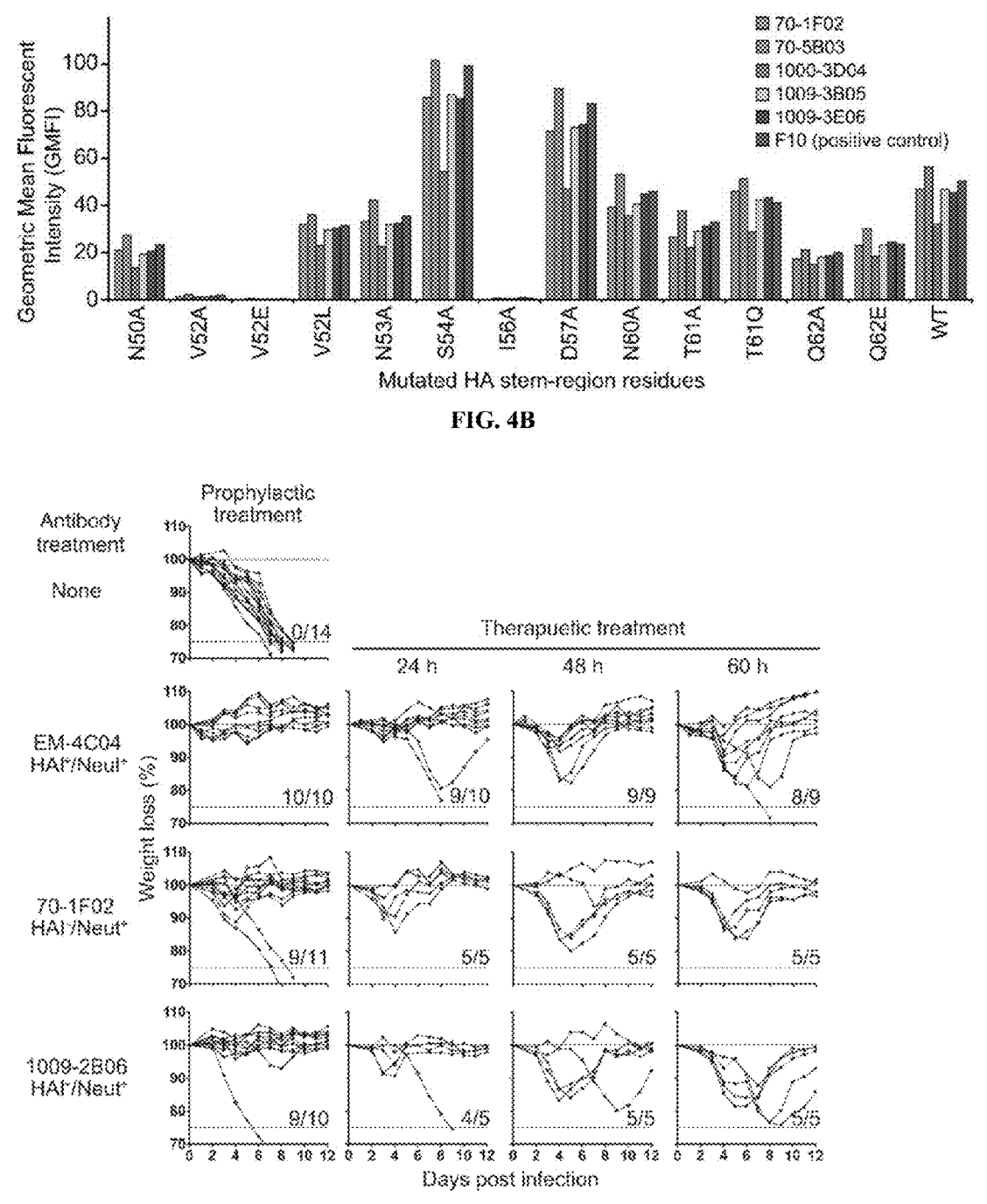

FIG. 4A, competition ELISA assays were used to determine the similarity in specificity between the various neutralizing antibodies. Shown is the percent competition of each antibody in an ELISA binding assay against all other neutralizing antibodies. A ten-fold molar excess of unlabeled antibody was used to inhibit a biotinylated antibody. Percent competition is calculated as the reduction in absorbance relative to the level of inhibition of any particular antibody against itself. Colors indicate degree of inhibition of antibody binding as indicated. Antibody C179 is a commercial antibody that binds to the stalk region of the HA molecule identifying epitope-1. Epitope-2 and -3 are each on the HA-head active site. 1000-2G06 and the non-neutralizing but HA binding antibodies had no competition with any of the other HA-reactive antibodies and are therefore not shown. VH gene usage of the individual antibodies is listed on the right. All assays were performed in duplicate. In FIG. 4B, plasmids encoding full-length wild type (WT) H5-TH04 (A/Thailand/2-SP-33/2004 (H5N1)) and its mutants were transiently transfected into 293T cells. 24 hours after transfection, cells were harvested for FACS analysis, and binding of indicated antibodies were tested at 10 μg/mL. The cell surface HA expression of each of the mutants were verified with a ferret anti-H5N1 serum (data not shown). Antibody F10 was one of the antibodies used to characterize the HA-stalk epitope by X-ray crystallography (Sui, 2009) and served as a positive control for the binding pattern expected of HA stalk reactive antibodies to these HA mutants.

FIG. 5. In vivo prophylactic and therapeutic efficacy of human mAbs against pandemic H1N1 influenza virus. 6-8 week old Balb/c mice were infected with a 3×LD50 dose of highly pathogenic, mouse-adapted 2009 pandemic H1N1 influenza (A/California/04/09). 24, 48 and 60 hours after infection 200 ug (10 mg/kg of body weight) of EM-4C04, 70-F02 or 1009-3B06 human mAb were injected intraperitoneally. All mice were monitored daily for body weight changes and any signs of morbidity and mortality. Percent of initial body weight is plotted and number of surviving mice is shown in the lower right of each plot. Infected, untreated mice showed clear signs of sickness around day 4-5 post-infection and perished by day 8-9. Prophylactic treatment is shown on the left for comparison. Antibody treatment conferred significant protection as determined by comparison of weights in untreated versus prophylaxis, and at the time of treatment versus 12 days post-infection (unpaired, two-tailed students t-test p<0.05). The log-rank test indicated significant survival as well (p<0.001). Figure shows one representative experiments of at least three independent repeat experiments.

Figure 6:
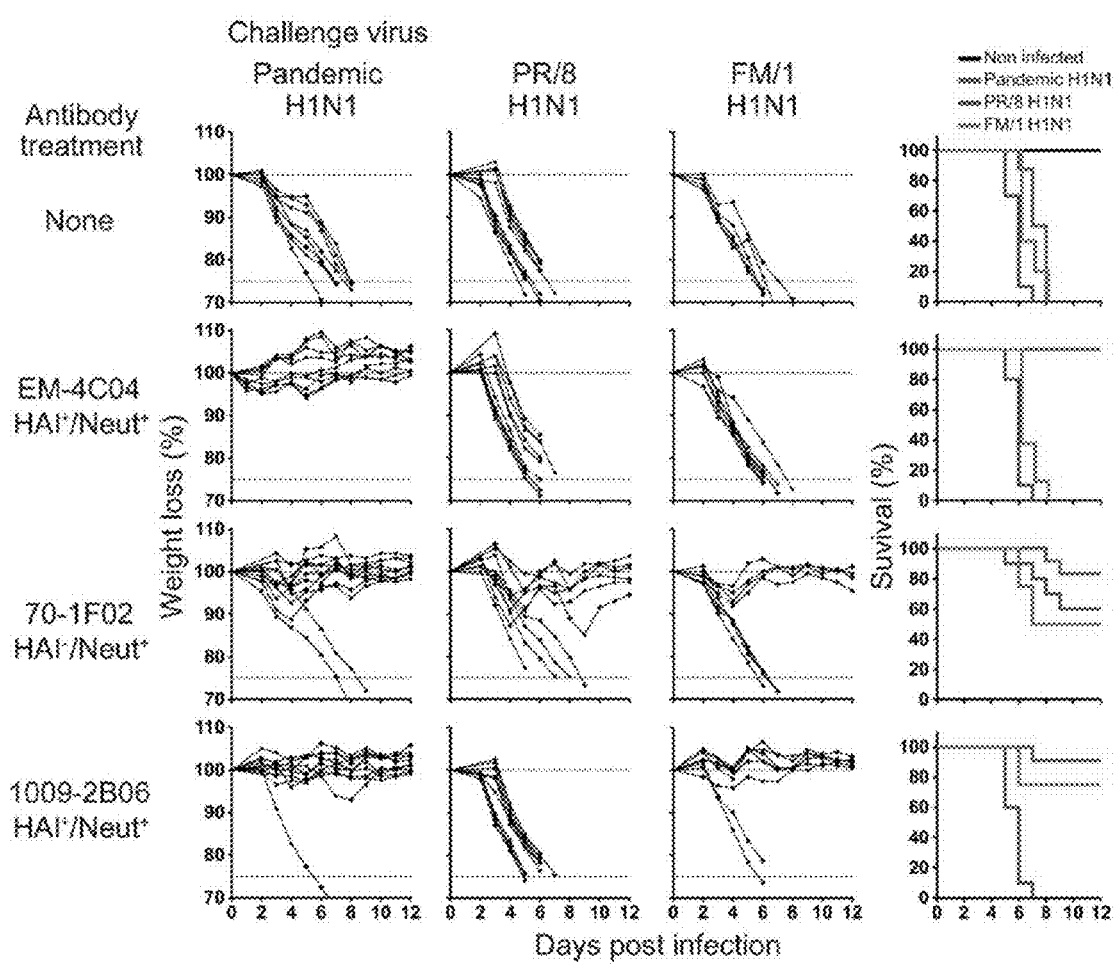

FIG. 6. Breadth of in vivo prophylactic efficacy in mice. 6-8 week old Balb/c mice were treated with 200 ug (10 mg/kg of body weight) EM-4C04, 70-1F02 or 1009-3B06 human mAb intra-peritoneally, Control mice were treated with PBS only, a control mAb or polyclonal human IgG. 12 hours later they were challenged with a 3×LD50 dose of mouse adapted pandemic H1N1, PR/8/34 or FM/1/47 influenza virus. All mice were monitored daily for body weight changes and any signs of morbidity and mortality. Percent of initial body weight (left) and survival curves (right) are plotted. Infected, untreated mice showed clear signs of sickness around day 4-5 post infection and perished by day 8-9. Figure shows one representative experiments of at least three independent repeat experiment. Antibody treatment conferred significant protection as determined by comparison of weights in untreated versus prophylaxis, and at the time of treatment versus 12 days post-infection (unpaired, two-tailed students t-test p<0.05). The log-rank test indicated significant survival as well (p<0.003).

FIG. 7A, Naïve antibody cross-reactivity levels were used to establish thresholds for scoring antibodies as positive against the pandemic H1N1 influenza strains. A set of 48 naïve antibodies were screened by ELISA for binding to the pandemic H1N1 influenza strain at concentrations beginning at 10 ug/ml and three 3-fold dilutions (the same initial concentration used to test the anti-H1N1 plasmablast antibodies). We assigned the minimum binding threshold at 2 standard deviations (2×SD) above the mean absorbance for the naïve antibodies at 10 ug/ml (left). Overall binding of curves of the naïve antibodies relative to this threshold are also provided. All ELISA assays were performed in duplicate.

Figure 7B:
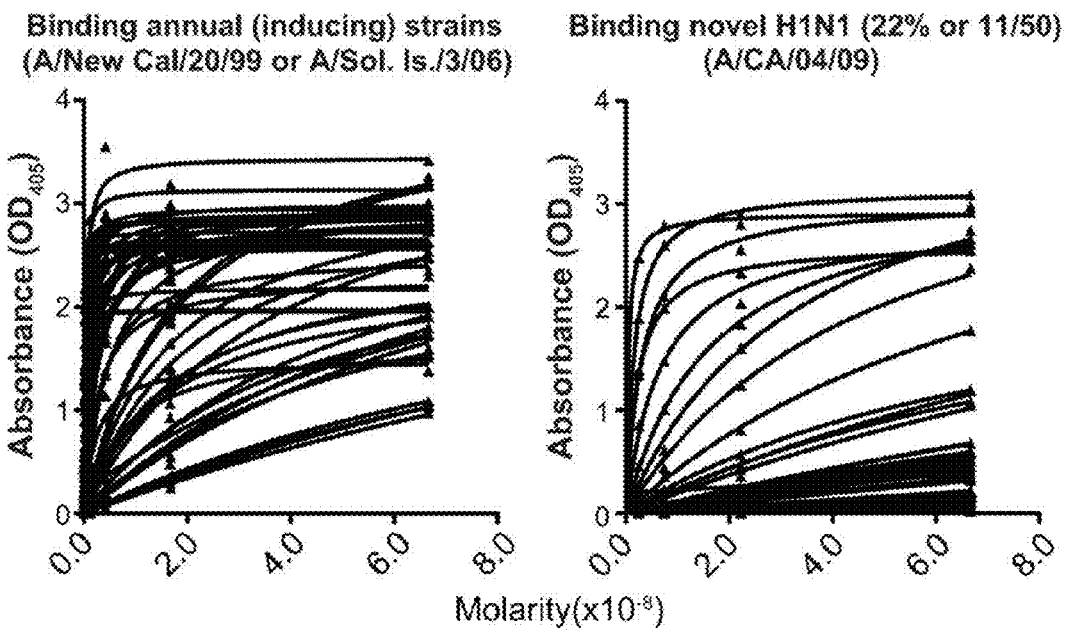

FIG. 7B, annual vaccine induced antibodies generated against past influenza strains prior to the 2009 pandemic H1N1 pandemic are only approximately one-third (22%) as likely to cross-react with the pandemic H1N1 strain than the inverse (FIGS. 2A and 2B, 63% of the pandemic H1N1-induced antibodies cross-react with past annual strains). We had generated 50 mAbs following annual vaccination prior to the pandemic. Binding of these pre-pandemic mAbs to annual strains is presented in the left panel and to the pandemic H1N1 strain on the right panel. These analyses were performed at least twice.

FIG. 8A, ELISA binding curves for multiple recombinant HA proteins and whole purified virus from different influenza strains for the 11 mAbs that neutralize pandemic H1N1 infectivity in vitro. These data were used for the summary analysis in FIG. 3 panels A and C. The ELISA assays were perform at least twice.

FIG. 8B, Antibody avidities were determined by Biacore Surface Plasmon Resonance (SPR) and ELISA. Antibodies 1009-3B06, 1000-3E01, and 1000-2G06 could not be determined because these mAbs did not bind to the recombinant HA protein from baculovirus sufficiently well for SPR. Avidities for these mAbs and for the antibodies that did not neutralize infection in vitro were estimated by Scatchard plot analyses of ELISA data (shown in parentheses). Three replicates were performed for the SPR analyses.

FIG. 9A, similar to the results based on mutations averaged by donor, mutation frequency considered by each individual VH gene are also particularly high in the pandemic H1N1 patient plasmablast samples, comparable to annual influenza and repeated anthrax-booster responses.

Figure 9B:
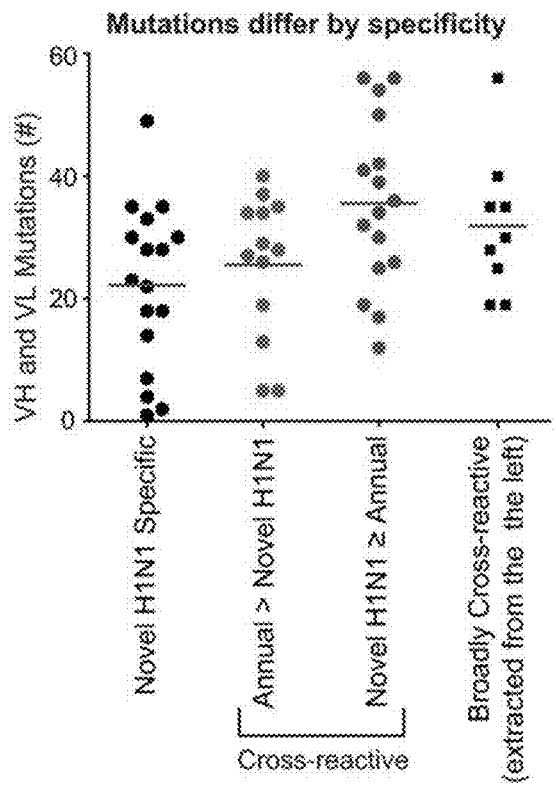

FIG. 9B shows an analysis of the variable gene repertoire indicated that cross-reactive antibodies binding pandemic H1N1 better than annual H1N1 strains have significantly more combined VH and VL mutations, suggesting accumulation after further affinity maturation of memory cells. Extraction of mutation numbers from the broadly cross-reactive antibodies indicates that in general they are from highly mutated variable genes as well. Statistical comparisons were made using student's t tests. The data points (variable genes) are grouped by hypothetical origins as described in the text. In total, the variable genes encoding cross-reactive antibodies as a single grouping also had significantly more somatic mutations than the pandemic H1N1 specific antibody genes (p=0.03). The frequency of mutations was significantly greater than the IgG controls for all donors except EM (t-test p<0.05).

Figure 10:
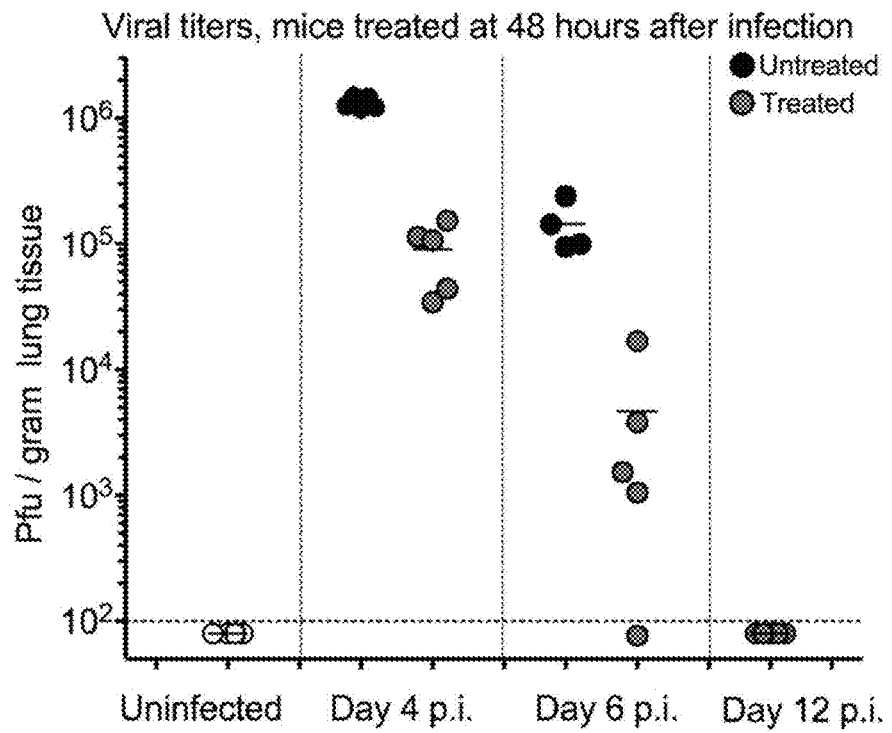

FIG. 10. Therapeutic control of pandemic H1N1 viral titers in lungs after mAb treatment. 6-8 week old Balb/c mice were infected with a lethal 3×LD50 dose of mouse adapted pandemic H1N1 and treated with 200 ug given i.p. EM4C04 48 hours later. Lung tissue was removed from groups of 5 mice per timepoint at 4, 6 and 12 days post infection. Lung viral titers were determined by plaque assay on MDCK cells and are reported as pfu per gram tissue.

FIG. 11 shows table 2 with detailed information about the 70-5B03 antibody that was confirmed to bind influenza. Each antibody is identified in Col. A by antibody name and an indication of whether the heavy or light chain is being described. Heavy chains are indicated by H1, H2 or H3 and light chains are indicated by K1, K2, K3 or K4 at the end of the identifier in Col. A. Col. B indicates whether the clone was productive. Col. C provides the V gene and V gene allele; Col. E provides the J gene and J allele. Col. E provides the D gene and allele (for heavy chains). Col. F provides the V-D-J region amino acid sequence (for heavy chains) (SEQ ID NO: 22). Col. G provides the V-J region amino acid sequence (for light chains) (SEQ ID NO: 23. Col. H provides the V-region amino acid sequence (SEQ ID NO: 24 and SEQ ID NO: 25). Col. I provides the FR1 amino acid sequence (SEQ ID NO: 26 and SEQ ID NO: 27). Col. J provides the CDR1 amino acid sequence(SEQ ID NO: 28 and SEQ ID NO: 29). Col. K provides the FR2 amino acid sequence (SEQ ID NO: 30 and SEQ ID NO: 31). Col. L provides the CDR2 amino acid sequence (SEQ ID NO: 32 and SEQ ID NO: 33). Col. M provides the FR3 amino acid sequence (SEQ ID NO: 34 and SEQ ID NO: 35). Col. N provides the CDR3 amino acid sequence (SEQ ID NO: 36 and SEQ ID NO: 37). Col. 0 provides the JUNCTION amino acid sequence (SEQ ID NO: 38 and SEQ ID NO: 39). Col. P provides the J-region amino acid sequence (SEQ ID NO: 40 and SEQ ID NO: 41). Col. Q provides the FR4 amino acid sequence (SEQ ID NO: 42 and SEQ ID NO: 43).

DETAILED DESCRIPTION

The present invention provides antibodies, including human and/or humanized forms, as well as fragment, derivatives/conjugates and compositions thereof that bind to an HA domain of the H1N1 influenza virus. Certain of the antibodies can neutralize multiple H1N1 strains and certain antibodies can neutralize multiple H1N1 and H5N1 strains. Anti-influenza antibodies are also herein referred to as antibodies of the invention.

As used herein, the terms "antibody" and "antibodies", also known as immunoglobulins, encompass monoclonal antibodies (including full-length monoclonal antibodies), spolyclonal antibodies, multispecific antibodies formed from at least two different epitope binding fragments (e.g., bispecific antibodies), human antibodies, humanized antibodies, camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Antibodies may be derived from any mammal, including, but not limited to, humans, monkeys, pigs, horses, rabbits, dogs, cats, mice, etc., or other animals such as birds (e.g. chickens).

Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains (CH). Each light chain has a variable domain at one end (VL) and a constant domain (CL) at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK.

The antibodies of the invention include full length or intact antibody, antibody fragments, native sequence antibody or amino acid variants, human, humanized, post-translationally modified, chimeric or fusion antibodies, immunoconjugates, and functional fragments thereof. The antibodies can be modified in the Fc region to provide desired effector functions or serum half-life. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity (CDC), or by recruiting nonspecific cytotoxic cells that express one or more effector ligands that recognize bound antibody on a influenza cell and subsequently cause phagocytosis of the influenza cell in antibody dependent cell-mediated phagocytosis (ADCP), or some other mechanism. Alternatively, where it is desirable to eliminate or reduce effector function, so as to minimize side effects or therapeutic complications, certain other Fc regions may be used. The Fc region of the antibodies of the invention can be modified to increase the binding affinity for FcRn and thus increase serum half-life. Alternatively, the Fc region can be conjugated to PEG or albumin to increase the serum half-life, or some other conjugation that results in the desired effect.

Naturally-occurring antibodies are immunoglobulin molecules comprised of four polypeptide chains, two heavy (H) chains and two light (L) chains inter-connected by disulfide bonds. Each heavy chain is comprised of a heavy chain variable region (VH) and a heavy chain constant region. The heavy chain constant region is comprised of three domains, CH1, CH2 and CH3. Each light chain is comprised of a light chain variable region (VL) and a light chain constant region. The light chain constant region is comprised of one domain, CL. The VH and VL regions can be further subdivided into regions of hypervariability, called complementarity determining regions (CDR), interspersed with regions that are more conserved, called framework regions (FR). Each VH and VL is composed of three CDRs and four FRs, arranged from amino-terminus to carboxy-terminus in the following order: FR1, CDR1, FR2, CDR2, FR3, CDR3, FR4.

CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

Each CDR can included amino acid residues from a complementarity determining region as defined by Kabat (i.e. about residues 24-34 (CDR-L1), 50-56 (CDR-L2) and 89-97 (CDR-L3) in the light chain variable domain (SEQ ID NO:1) and 31-35 (CDR-H1), 50-65 (CDR-H2) and 95-102 (CDR-H3) in the heavy chain variable domain (SEQ ID NO:2); Kabat et al., Sequences of Proteins of Immunological Interest, 5th Ed. Public Health Service, National Institutes of Health, Bethesda, Md. (1991)) and/or those residues from a hypervariable loop (i.e. about residues 26-32 (CDR-L1), 50-52 (CDR-L2) and 91-96 (CDR-L3) in the light chain variable domain (SEQ ID NO:1) and 26-32 (CDR-H1), 53-55 (CDR-H2) and 96-101 (CDR-H3) in the heavy chain variable domain (SEQ ID NO:2); Chothia and Lesk J. Mol. Biol. 196:901-917 (1987)). In some instances, a complementarity determining region can include amino acids from both a CDR region defined according to Kabat and a hypervariable loop.

Framework regions are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) of SEQ ID NO:1) and the heavy chain FR residues are positioned about at residues 1-30 (HCFR1), 36-49 (HCFR2), 66-94 (HCFR3), and 103-113 (HCFR4) of SEQ ID NO:2. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain (SEQ ID NO:1) and the heavy chain FR residues are positioned about at residues 1-25 (HCFR1), 33-52 (HCFR2), 56-95 (HCFR3), and 102-113 (HCFR4) in the heavy chain (SEQ ID NO:2). In some instances, when the CDR comprises amino acids from both a CDR as defined by Kabat and those of a hypervariable loop, the FR residues will be adjusted accordingly.

An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

Single-chain Fv or (scFv) antibody fragments comprise the VH and VL domains of antibody, wherein these domains are present in a single polypeptide chain. Generally the Fv polypeptide further comprises a polypeptide linker between the VH and VL domains, which enables the scFv to form the desired structure for antigen binding.

Diabodies are small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites.). Linear antibodies comprise a pair of tandem Fd segments (VH-CH1-VH-CH1) which, together with complementary light chain polypeptides, form a pair of antigen binding regions. Linear antibodies can be bispecific or monospecific.

The antibodies herein specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An antigen binding portion of an antibody specifically binds to an antigen (e.g., H1N1). It has been shown that the antigen-binding function of an antibody can be performed by portions of a full-length antibody, all of which are encompassed by the general term antibody, including: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al, (1989) Nature 341:544 546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Single chain Fv and other forms of single chain antibodies, such as diabodies are also encompassed by the general term antibody. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444; Poljak et al. (1994) *Structure* 2:1121).

An antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) *Human Antibodies and Hybridomas* 6:93) and use of a cysteine residue, a marker peptide and a C-terminal polyhistidine tag to make bivalent and biotinylated scFv molecules (Kipriyanov et al. (1994) *Mol. Immunol.* 31:1047). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

Human antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs and in particular CDR3. Recombinant antibodies are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (Taylor et al. (1992) Nucl. Acids Res. 20:6287) or antibodies prepared, expressed, created or isolated by any other means that involves splicing of human immunoglobulin gene sequences or variants thereof to other DNA sequences. Such recombinant human antibodies have variable and constant regions derived from human germline immunoglobulin sequences or variants thereof. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that may not naturally exist within the human antibody germline repertoire in vivo.

In certain embodiments, the anti-influenza antibodies are isolated and/or purified and/or pyrogen free antibodies. The term "purified" as used herein, refers to other molecules, e.g. polypeptide, nucleic acid molecule that have been identified and separated and/or recovered from a component of its natural environment. Thus, in one embodiment the antibodies of the invention are purified antibodies wherein they have been separated from one or more components of their natural environment.

The anti-influenza antibodies of the invention immunospecifically bind an epitope specific to an HA domain of an H1N1 influenza virus and do not specifically bind to other polypeptides. The term "epitope" as used herein refers to a protein determinant capable of binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The present anti-influenza antibodies comprise at least one antigen binding domain that comprises at least one complementarity determining region (CDR1, CDR2 and CDR3). In one embodiment, the anti-influenza antibodies comprise a VH that comprises at least one VH CDR (e.g., CDR-H1, CDR-H2 or CDR-H3). In another embodiment, the anti-influenza antibodies comprise a VL that comprises at least one VL CDR (e.g., CDR-L1, CDR-L2 or CDR-L3).

In certain embodiments, the anti-influenza antibodies comprise a VH CDR1 having an amino acid sequence identical to or comprising 1, 2, or 3 amino acid residue substitutions relative to a VH CDR1 in column J of Table 2, a VH CDR2 having an amino acid sequence identical to or comprising 1, 2, or 3 amino acid residue substitutions relative to a VH CDR2 in column L of Table 2 and a VH CDR3 having an amino acid sequence identical to or comprising 1, 2, or 3 amino acid residue substitutions relative to a VH CDR3 in column N of Table 2. In another embodiment, the anti-influenza antibodies comprise a VL CDR1 having an amino acid sequence identical to or comprising 1, 2, or 3 amino acid residue substitutions relative to a VL CDR1 in column J of Table 2, a VL CDR2 having an amino acid sequence identical to or comprising 1, 2, or 3 amino acid residue substitutions relative to a VL CDR2 in column L of Table 2, and a VL CDR3 having an amino acid sequence identical to or comprising 1, 2, or 3 amino acid residue substitutions relative to a VL CDR3 in column N of Table 2.

In certain embodiments, the anti-influenza antibodies comprise a VH CDR1 having an amino acid sequence identical to a VH CDR1 in column J of Table 2, a VH CDR2 having an amino acid sequence identical to a VH CDR2 in column L of Table 2 and a VH CDR3 having an amino acid sequence identical to a VH CDR3 in column N of Table 2. In another embodiment, the anti-influenza antibodies comprise a VL CDR1 having an amino acid sequence identical to a VL CDR1 in column J of Table 2, a VL CDR2 having an amino acid sequence identical to a VL CDR2 in column L of Table 2; and a VL CDR3 having an amino acid sequence identical to a VL CDR3 in column N of Table 2. In certain embodiments the VH and VL CDRs are all from the same antibody in Table 2.

In certain embodiments, the anti-influenza antibodies comprise a heavy chain V-region having an amino acid sequence identical to a heavy chain V-region in column H of Table 2 and a light chain V-region identical to a light chain V-region in column H of Table 2.

In certain embodiments, the anti-influenza antibodies comprise a heavy chain V-region having an amino acid sequence identical to or having 1, 2, 3, 4, 5, 6, 7, 8, 9 or 10 amino acid substitution relative to a heavy chain V-region in column H of Table 2 and a light chain V-region having an amino acid sequence identical to or having 1, 2, 3, 4, 5, 6, 7, 8, 9 or 10 amino acid substitution relative to a light chain V-region in column H of Table 2

In certain embodiments, the anti-influenza antibodies comprise a heavy chain VDJ-region having an amino acid sequence identical to a heavy chain VDJ-region in column F of Table 2 and a light chain VJ-region identical to a light chain VJ-region in column G of Table 2

In certain embodiments, the anti-influenza antibodies comprise a heavy chain VDJ-region having an amino acid sequence identical to or having 1, 2, 3, 4, 5, 6, 7, 8, 9 or 10 amino acid substitution relative to a heavy chain VDJ-region in column F of Table 2 and a light chain VJ-region having an amino acid sequence identical to or having 1, 2, 3, 4, 5, 6, 7, 8, 9 or 10 amino acid substitution relative to a light chain VJ-region in column G of Table 2.

In addition to the amino acid sequences described above, the invention further provides nucleotide sequences corresponding to the amino acid sequences and encoding for the human, humanized and/or chimeric antibodies of the invention. In one embodiment, the invention provides polynucleotides comprising a nucleotide sequence encoding an anti-influenza antibody described herein or fragments thereof These include, but are not limited to, nucleotide sequences that code for the above referenced amino acid sequences. Thus, the present invention also provides polynucleotide sequences encoding VH and VL framework regions including CDRs and FRs of antibodies described herein as well as expression vectors for their efficient expression in cells (e.g. mammalian cells).

In one embodiment, the anti-influenza antibodies immunospecifically bind an HA domain of an H1N1 influenza virus or antigenic fragments thereof, having at least 60%, 65%, 70%, 75%, 80%, 85%, 90%, 95% or having at least 100% identity to the amino acid sequence of an antibody described herein. In a further embodiment, the anti-influenza antibodies immunospecifically bind to an HA domain of an H1N1 influenza virus polypeptide or antigenic fragments thereof, having at least 90%, 91%, 92%, 93%, 94%, 95%, 96%, 97%, 98%, 99% or having at least 100% identity to the amino acid sequence of an antibody described herein.

Methods for producing and screening for specific antibodies using recombinant DNA technology are routine and well known in the art (e.g. U.S. Pat. No. 4,816,567). DNA encoding the monoclonal antibodies may be readily isolated and/or sequenced using conventional procedures (e.g., by using oligonucleotide probes that are capable of binding specifically to genes encoding the heavy and light chains of murine antibodies). Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells.

Review articles on recombinant expression in bacteria of DNA encoding the antibody include Skerra et al., Curr. Opinion in Immunol., 5:256-262 (1993) and Pluckthun, Immunol. Revs., 130:151-188 (1992). As described below for antibodies generated by phage display and humanization of antibodies, DNA or genetic material for recombinant antibodies can be obtained from source(s) other than hybridomas to generate antibodies of the invention.

Recombinant expression of an antibody or variant thereof generally requires construction of an expression vector containing a polynucleotide that encodes the antibody. The invention, thus, provides replicable vectors comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Once the expression vector is transferred to a host cell by conventional techniques, the transfected cells are then cultured by conventional techniques to produce an antibody. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In one embodiment, human cell lines developed by immortalizing human lymphocytes can be used to recombinantly produce monoclonal antibodies. In one embodiment, the human cell line PER.C6. (Crucell, Netherlands) can be used to recombinantly produce monoclonal antibodies.

Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae, Pichia*, U.S. Pat. No. 7,326,681; etc), plants cells (US20080066200); and chicken cells (WO2008142124).

Once an antibody molecule has been produced by recombinant or hybridoma expression, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences (referred to herein as "tags") described above or otherwise known in the art to facilitate purification.

It is known that variants of the Fc region (e.g., amino acid substitutions and/or additions and/or deletions) enhance or diminish effector function of the antibody (See e.g., U.S. Pat. Nos. 5,624,821; 5,885,573; 6,538,124; 7,317,091; 5,648, 260; 6,538,124; WO 03/074679; WO 04/029207; WO 04/099249; WO 99/58572; US Publication No. 2006/0134105; 2004/0132101; 2006/0008883) and may alter the pharmacokinetic properties (e.g. half-life) of the antibody (see, U.S. Pat. Nos. 6,277,375 and 7,083,784). Thus, in certain embodiments, the anti-influenza antibodies of the invention comprise an altered Fc region (also referred to herein as "variant Fc region") in which one or more alterations have been made in the Fc region in order to change functional and/or pharmacokinetic properties of the antibodies. The serum half-life of proteins comprising Fc regions may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time (MRT) in circulation for the antibody administered. In a specific embodiment, the present invention provides an Fc variant antibody, wherein the Fc region comprises at least one non-naturally occurring amino acid at one or more positions selected from the group consisting of 252, 254, and 256. In one embodiment, the non-naturally occurring amino acids are selected from the group consisting of 252Y, 254T and 256E.

In certain embodiments, the anti-influenza antibodies and compositions thereof of the invention may be used in vivo and/or in vitro for diagnosing H1N1 influenza associated diseases. This can be achieved, for example, by contacting a sample to be tested, optionally along with a control sample, with the antibody under conditions that allow for formation of a complex between the antibody and H1N1 influenza. Complex formation is then detected (e.g., using an ELISA). When using a control sample along with the test sample, complex is detected in both samples and any statistically significant difference in the formation of complexes between the samples is indicative of the presence of influenza in the test sample.

In one embodiment, the invention provides a method of determining the presence of influenza in a sample suspected of containing influenza, said method comprising exposing the sample to an anti-influenza antibody of the invention, and determining binding of the antibody to the H1N1 influenza virus in the sample wherein binding of the antibody to the H1N1 influenza virus in the sample is indicative of the presence of the H1N1 influenza virus in the sample. In one embodiment, the sample is a biological sample. In another embodiment, the sample is a nasopharyngeal wash.

In certain embodiments, the anti-influenza antibodies and compositions thereof of the invention may be administered for prevention and/or treatment of influenza disease caused by an H1N1 influenza infection. The invention encompasses methods of preventing, treating, ameliorating a symptom of, or reducing the risk of an influenza-mediated infection, disease or disorder, wherein the methods comprise administering anti-influenza antibodies of the invention.

EXAMPLES

Described below is an analysis of plasmablast and monoclonal antibody responses induced by pandemic H1N1 infection in humans. Unlike antibodies elicited by annual influenza vaccinations, most neutralizing antibodies induced by pandemic H1N1 infection were broadly cross-reactive against epitopes in the hemagglutinin (HA) stalk and head domain of multiple influenza strains. The antibodies were from cells that had undergone extensive affinity maturation. Thus, it is possible that the plasmablasts producing these broadly neutralizing antibodies were predominantly derived from activated memory B cells specific for epitopes conserved in several influenza strains. Consequentially, most neutralizing antibodies were broadly reactive against divergent H1N1 and H5N1 influenza strains. Certain of the antibodies generated potently protected and rescued mice from lethal challenge with pandemic H1N1 or antigenically distinct influenza strains.

Influenza-Specific Plasmablasts are Persistently Induced Throughout Infection Providing a Rich Source of Antiviral mAbs.

The B cell responses were examined in nine patients infected with the pandemic 2009 H1N1 influenza virus. These patients had a varying course and severity of disease. The cases ranged from mild disease with rapid viral clearance within a few days after onset of symptoms, to severe cases that shed virus for several weeks and required hospitalization with ventilator support. A majority of the patients were treated with antiviral drugs. The diagnoses were confirmed by pandemic H1N1 specific RT-PCR and serology. All patients had neutralizing titers of serum antibodies at the time of blood collection. A summary of the clinical patient data is shown in Table 1. The majority of samples were obtained around 10 days after the onset of symptoms, with the exception of a particularly severe case where sampling was done 31 days after symptom onset. Antigen specific plasmablasts appear transiently in peripheral blood after vaccination with influenza or other vaccines (Bemasconi et al., 2002; Brokstad et al., 1995; Sasaki et al., 2007; Wrammert et al., 2008), but the kinetics of their appearance and persistence during an ongoing infection remain unclear. Here we have analyzed the magnitude and specificity of the plasmablast response in blood samples taken within weeks after onset of clinical symptoms of pandemic H1N1 influenza virus infection. Using a virus-specific ELISPOT assay, we could show a significant number of pandemic H1N1 reactive plasmablasts in the blood of the infected patients, while none were detectable in a cohort of healthy volunteers (FIGS. 1A and 1B).

These cells were also readily detectable in the more severe cases, several weeks after symptom onset. FIGS. 1A and 1C illustrates that of the total IgG secreting cells over half of the cells were producing antibodies that bound pandemic H1N1 influenza virus. Moreover, plasmablasts specific for HA occurred at 30-50% the frequency of virus-specific cells (FIGS. 1C and D), the specificity most likely to be critical for protection. Most patients also had a relatively high frequency of plasmablasts making antibodies that bound to past, seasonal influenza strains (FIG. 1C) or indeed recombinant HA from the previous annual H1N1 strain, A/Brisbane/59/2007. Based on the overall frequency of pandemic H1N1 specific cells it is likely that the cells binding other strains were -lapping populations and cross-reactive. None of the induced plasmablast cells bound to recombinant HA from the H3N2 strain from the same vaccine (A/Brisbane/10/2007). These findings demonstrate that influenza-specific human plasmablasts are continuously generated throughout an ongoing infection and that a fairly high proportion of these cells makes antibodies that also cross-react with previous None of the induced plasmablast cells bound to recombinant HA from the H3N2 strain from the same vaccine (A/Brisbane/10/2007). These findings demonstrate that influenza-specific human plasmablasts are continuously generated throughout an ongoing infection and that a fairly high proportion of these cells make antibodies that also cross-react with previous annual H1N1 influenza strains.

In order to analyze the specificity, breadth and neutralizing capacity of these plasmablasts, we used single-cell PCR to amplify the heavy and light chain variable region genes from individually sorted cells (defined as $CD19^+$, $CD20^{lo/-}$, $CD3^-$, $CD38^{high}$, $CD27^{high}$ cells) (FIG. 1E) (Smith et al., 2009; Wrammert et al., 2008). These genes were cloned and expressed as mAbs in 293 cells and the antibodies screened for reactivity by ELISA. Thresholds for scoring antibodies as specific to the influenza antigens were empirically determined based on being two standard-deviations greater than the background level of binding evident from 48 naïve B cell antibodies (detailed in FIG. 7A). Of 86 antibodies generated in this fashion, 46 (53%) bound pandemic H1N1 (FIG. 1F) and one third (15

TABLE I

Summary of clinical data for patients with acute pandemic H1N1 virus infections

| Patient | Age | Gender | HAI titer | MN titer | Co-morbidities | Initial symptoms | Hospital course | Sample collection | Antiviral treatment |
|---|---|---|---|---|---|---|---|---|---|
| EM | 30 | F | 640 | 1280 | none | Fever, cough, dyspnea | Acute respiratory distress syndrome, bacterial pneumonia, pulmonary embolism, prolonged oscillatory ventilator support, tracheostomy, discharged after 2 mo | Day 31 | Oseltamivir |
| 1000 | 37 | M | 80 | 40 | Hypertension, interstitial | Fever, cough, shortness of breadth, nausea, | Pneumonia, acute sinusitus, acute renal failure, discharged | Day 18 | Oseltamivir, Zanamavir |

TABLE I-continued

Summary of clinical data for patients with acute pandemic H1N1 virus infections

| Patient | Age | Gender | HAI titer | MN titer | Co-morbidities | Initial symptoms | Hospital course | Sample collection | Antiviral treatment |
|---|---|---|---|---|---|---|---|---|---|
| | | | | | lung disease of unknown etiology | vomiting | after 8 d | | |
| 70 | 38 | F | 80 | 160 | none | Fever, cough, body aches | N/A | Day 15 | None |
| 1009 | 21 | M | 20 | 20 | Congenital heart disease, repair for Tetralogy of Fallot | Fever, cough, sore throat, nausea, diarrhea | N/A | Day 9 | Oseltamivir |
| 1010 | 24 | M | 10 | 10 | none | Fever, cough, nausea, vomiting, diarrhea | N/A | Day 11 | Oseltamivir |
| 1011 | 25 | M | 20 | 10 | none | Fever, cough, sore throat, vomiting, headache, confusion | N/A | Day 9 | Oseltamivir |
| 1013 | 26 | M | 80 | 160 | none | Fever, cough, sore throat, body aches, nausea, vomiting, diarrhea | N/A | Day 9 | None |
| 1014 | 45 | F | 80 | 20 | none | Fever, chills, cough, sore throat, body aches, headache, nausea, vomiting | N/A | Day 9 | None |

[1]Indicates whether monoclonal antibodies were made from the plasmoblasts of these patients.

antibodies) were reactive to HA (FIG. 1G and FIG. 8A), most of them at sub-nanomolar avidities (based on surface plasmon resonance analyses, FIG. 8B). On a per donor basis, 55% of the mAbs bound to purified pandemic H1N1 virions (range: 33% to 77%). Of the virus-specific antibodies 31% bound to recombinant HA (range: 14% to 55%). We conclude that virus-specific plasmablasts are readily detected after pandemic H1N1 influenza virus infection and that virus-specific human mAbs can be efficiently generated from these cells.

Plasmablasts from Patients Infected with Pandemic H1N1 Influenza were Highly Cross-Reactive to Pre-Pandemic Influenza Strains As the plasmablasts are specifically induced by the ongoing immune response, we can learn about the origin of the B cells activated by pandemic H1N1 infection. Consistent with the frequency of plasmablasts secreting antibodies binding annual influenza strains by ELISPOT analyses (FIG. 1C), a majority (29/46 or 63%) of the pandemic H1N1-specific antibodies also cross-reacted with seasonal influenza viruses (FIGS. 2A and 2B). In fact, by ELISA, one third of these antibodies bind to the pre-pandemic strains at lower concentrations than they did to the pandemic H1N1 strain, suggesting higher avidity binding. By comparison, only 22% (11/50) of plasmablasts induced by annual H1N1 strains prior to the pandemic could bind the pandemic H1N1 influenza (FIG. 7B). We propose that the cross-reactivity of pandemic H1N1 induced cells derives from the activation of memory cells originally specific for past influenza immunizations in an original antigenic sin (OAS) fashion.

Evidence of extensive affinity maturation suggests a high frequency of memory cell activation against the pandemic H1N1 strain Based on the 10 to 15-fold induction of plasmablasts and expression of intracellular Ki67 during ongoing immune responses (Bemasconi et al., 2002; Brokstad et al., 1995; Sasaki et al., 2007; Smith et al., 2009; Wrammert et al., 2008) we can assume that most plasmablasts result from the ongoing infection or vaccine response. The ready detection of clonal expansions at an average frequency of 16.5% of the cells for the six patients supports this view (based on CDR3 sequence similarity, FIG. 2C). Since the discovery of somatic mutation it has been appreciated that mutations progressively accumulate on variable genes after repeated immunizations (McKean et al., 1984). Thus, we can gain insight into the origin of the pandemic H1N1 response by comparing the somatic mutation frequency of the plasmablasts present during H1N1 infection to that of other plasmablast responses. The PCR strategy allowed isolation of either IgG or IgA transcripts and identified 68% IgG and 32% IgA plasmablasts from the patients. Similar to plasmablasts induced by annual vaccination (Wrammert et al., 2008), or after a 4th booster vaccine to anthrax, the variable genes of novel H1N1-induced cells from five of the six patients harbored high numbers of somatic mutations (averaging >19 per patient, FIG. 2D and FIG. 9A). For these 5 patients mutations had accumulated significantly more than from primary IgG plasmablast responses to anthrax or vaccinia (small pox) vaccines, and more so than for IgG positive memory B cells from our historical data that averaged 14/VH gene (Koelsch et al., 2007; Wrammert et al., 2008; Zheng et al., 2005; Zheng et al., 2004) (t-test p<0.05, FIG. 2C and FIG. 9B) or from 347 IgG memory cell sequences previously published by another group (averaging 15/VH gene) (de Wildt et al., 2000). Interestingly, for patient EM (outlier in FIG. 2D) who had the most severe infection (Table 1), mutations had accumulated at a significantly lower frequency than the IgG controls (FIG. 9A, p<0.0001), suggesting a unique circumstance such as a low-level or lacking primary response. Though based on a limited number of patients, the frequent cross-reactivity and high number of somatic mutations support a model in which many of the plasmablasts induced by pandemic H1N1 infection arose from cross-reacting memory B cells.

A majority of the neutralizing antibodies bound to highly conserved epitopes in both the HA stalk and head regions.

A high frequency of the HA-specific antibodies was able to neutralize the virus in vitro (totaling 73% or 11/15, FIG. 3A). These neutralizing antibodies could be further categorized into two distinct groups: i) neutralizing antibodies that displayed HAI (hemagglutination inhibition) activity (HAI[+]), and ii) neutralizing antibodies that had no HAI activity, indicating that they bound to sites other than the HA active site. Interestingly, antibodies of the latter type were predominant in the response (FIG. 3A). This specificity is reminiscent of antibodies against the recently discovered broadly neutralizing epitopes found on the HA stalk, rather than those located on the HA globular head that is more typical for neutralizing antibodies (Ekiert et al., 2009; Sui et al., 2009). Importantly, five of these antibodies are indeed of similar specificity (including antibodies 70-5B03, 70-1F02, 1000-3D04, and a clonal pair from donor 1009: 3B05 and 3E06). These five antibodies bind with high affinity to most H1 strains including all from the vaccines of the past 10 years, the 1918 pandemic strain, and to the H5 of a highly pathogenic avian influenza strain (FIG. 3B and FIG. 8A). In addition, these five antibodies cross-compete for a similar epitope that was not over-lapping with the HAI+antibodies (epitope-1, FIG. 4A). These antibodies are competitively inhibited by a commercial antibody referred to as C179 that binds this HA-stalk region (Okuno et al., 1993), and four of five of these antibodies are encoded by the hallmark VH1-69 gene (Ekiert et al., 2009; Sui et al., 2009). To verify HA stalk reactivity these five antibodies were tested for binding to H5 variants predicted to affect the stalk-epitope by the crystal structure and their binding patterns compared to that of the prototypical stalk antibody (mAb F10, (Sui et al., 2009)) (FIG. 4B). Each H5 variant has a single residue mutation in the stalk region and was transiently expressed on 293T cells. FACS analysis showed that the five antibodies bound to all 13 H5 variants tested at levels quite similar to F10 for which a crystal structure had been generated to define this epitope. Thus, half of the neutralizing and a surprising 10% of all antibodies induced by pandemic H1N1 infection bound to a conserved, critical epitope on the HA stalk. By comparison, none of 50 H1N1 strain-specific antibodies that we had previously isolated after annual vaccination prior to the 2009 pandemic had this reactivity (data not shown). The frequency of pandemic induced stem reactive antibodies (5/46) versus those from annual vaccine (0/50) is significantly greater (Chi-square test p=0.02). Further, this specificity is only rarely seen in human memory B cells (Corti et al., 2010) or from phage-display libraries (Sui et al., 2009). These observations support the idea that a vaccine might be developed that preferentially influenzas the HA-stalk, thus providing broad protection against many influenza strains.

The remaining neutralizing antibodies were HAI+ and therefore bound to the HA-globular head. Based on cross-competition analyses these antibodies fell into two groups binding non-overlapping regions of the HA head including epitope-2 and epitope-3 (FIGS. 3B and 4A). Indeed, by spontaneous escape mutant selection, we found that the EM4C04 mAb binds to the Sa region of the HA globular head (unpublished data). Thus by proximity based on the competition assay (FIG. 4A), we can predict that all of the epitope-2 antibodies bind near the Sa/Sb region (including: EM-4C04, 1009-3B06, and 1009-3F01).

Broadly-reactive antibodies binding both pandemic H1N1 strains and common annual H1N1 strains have been identified both in humans (Krause et al.; Xu et al.) and in mice (Manicassamy et al., 2010). It is notable that three of five of the HA globular-head binding antibodies induced by pandemic H1N1 infection were also broadly-reactive to various H1N1 strains (FIG. 3B). One such novel antibody was the SF1009-3B06 antibody that reacts strongly with the pandemic H1N1 strain as well as all recent H1N1 vaccine strains (FIG. 3B and FIG. 8A). The precise epitope to which the 1009-3B06 antibody binds appears to be quite unique: it is only accessible on whole virions, not on recombinant HA, suggesting that the epitope is quaternary in nature. Finally, two antibodies cross-reacted and inhibited hemagglutination to all recent H1 vaccine strains and reacted strongly to the 1918 pandemic strain (antibodies 1009-3E04 and 1000-3E01, FIGS. 3B and 4A epitope-3). These mAbs bind to past vaccine strains with higher avidity than to the pandemic H1N1.

Only two of 11 neutralizing antibodies were highly specific for the pandemic H1N1 strain alone (FIG. 3B and FIG. 8A), including a low avidity antibody, 1000-2G06, that only showed slight neutralization capacity in vitro, and EM-4C04 that was very effective at neutralizing the pandemic H1N1 influenza. We conclude from these experiments that a surprising 82% (9/11) of the neutralizing plasmablasts that we isolated during pandemic H1N1 influenza infections were broadly cross-reactive to multiple influenza strains.

Potent in vivo protection and rescue of mice challenged with a lethal dose of pandemic H1N1 or antigenically distinct influenza virus strains.

There is a distinct interest in the world in developing monoclonal antibodies for use in a therapeutic setting. We selected three representative antibodies of the set we have identified for detailed functional analysis both in vitro (FIG. 3C) and in vivo (FIGS. 5 and 6), including: EM-4C04, 1009-3B06 and 70-1F02. As described above, the antibodies EM-4C04 and 1009-3B06 are specific for the active site of the HA molecule, whereas 70-1F02 binds to the stalk region. Furthermore, EM-4C04 is highly specific for pandemic H1N1 whereas 1009-3B06 and 70-F02 display broadly cross-reactive binding (FIG. 3B) and have functional activity against multiple recent and older H1N1 strains (FIG. 3C). These antibodies were all highly effective at providing prophylactic protection against infection with a lethal dose of mouse-adapted pandemic H1N1 in 6-8 week old Balb/c mice (FIG. 5). Moreover, all three antibodies were effective therapeutically, even when they were administered as late as 60 hours after the lethal challenge infection, well after the mice were symptomatic. For EM-4C04 we have successfully treated mice as far out as 72 hours post-infection (data not shown). Infected mice were already showing measurable weight loss that was reversed by administration of the antibody, demonstrating therapeutic potential even after the onset of disease. Viral clearance was analyzed in mice treated at 48 hours post infection with EM4C04 (FIG. 10). As early as day 4, the antibody-treated mice exhibited more than a log reduction in viral titers; titers continued to decline, such that by day 6, virus was undetectable or present at very low levels. The untreated mice perished by day 7 or 8 whereas the treated mice cleared the infection with no detectable virus on day 12. Finally, the two broadly-reactive antibodies, 1009-3B06 and 70-1F02 that showed activity against several current and older H1N1 seasonal influenza strains in vitro (FIG. 3C) were also tested in vivo against antigenically distinct influenza strains. For these experiments mice were treated with 200 ug of mAb intraperitoneally 12 hours prior to infection with a lethal dose of either pandemic H1N1 influenza or either of the two common influenza lab strains PR/8/34 or FM/1/47. 1009-3806 and 70-1F02 showed protection against these antigenically distinct H1N1 influenza strains, as illustrated in FIG. 5. EM-4C04, that is highly specific for the pandemic H1N1, had no protective effect on infection with PR/8/34 or FM/1/47. In conclusion, the antibodies characterized herein show promise for development as broadly reactive therapeutic agents against the pandemic H1N1 influenza virus as well as against the majority of H1N1 and H5N1 influenza strains.

Detailed Information Regarding Antibodies that Bind Influenza Virus

Table 2 (FIG. 11) provides detailed information on the antibody (70-5B03) that was confirmed to bind influenza. The antibody is identified in Col. A by antibody name and an indication of whether the heavy or light chain is being described. Heavy chains are indicated by H1, H2 or H3 and light chains are indicated by K1, K2, K3 or K4 at the end of the identifier in Col. A. Thus, line 2 of Table 2 describes 1000-1B02H, which is a heavy chain for one of the cloned antibodies, and line 3 of Table 2 describes 1000-1B02K2, which is the light chain for the same antibody. Col. B indicates whether the clone was productive; Col. C provides the V gene and V gene allele; Col. E provides the J gene and J allele. Col. E provides the D gene and allele (for heavy chains). Col. F provides the V-D-J region amino acid sequence (for heavy chains). Col. G provides the V-J region amino acid sequence (for light chains). Col. H provides the V-region amino acid sequence. Col. I provides the FR1 amino acid sequence. Col. J provides the CDR1 amino acid sequence. Col. K provides the FR2 amino acid sequence. Col. L provides the CDR2 amino acid sequence. Col. M provides the FR3 amino acid sequence. Col. N provides the CDR3 amino acid sequence.

The following techniques and materials were used in the studies described above.

Patients:

All studies were approved by the Emory University, University of Chicago and Columbia University institutional review boards (Emory IRB#22371 and 555-2000, U of C IRB#16851E, CU IRB#AAAE1819). Patient clinical information is detailed in Table 1.

PBMC and Plasma Isolation:

All work with samples from infected patients was performed in a designated BSL2+ facility at Emory University. Peripheral blood mononuclear cells (PBMC) were isolated using Vacutainer tubes (Becton Dickinson, BD), washed, and resuspended in PBS with 2% FCS for immediate use or frozen for subsequent analysis. Plasma samples were saved in −80C.

Viruses and Antigens:

The pandemic H1N1 influenza virus (A/California/04/2009) was kindly provided by Dr. Richard J Webby at St. Jude Childrens Hospital. Influenza virus stocks used for the assays were freshly grown in eggs, prepared and purified as described (Wrammert et al., 2008) and the hemagglutination activity (HA) was determined using turkey red blood cells (Lampire Biological Laboratories, Pipersville, Pa.) as previously described (Wrammert et al., 2008) or purchased as inactivated preparations (ProSpec-Tany TechnoGene Ltd., Rehovot, Israel) and included: A/California/04/09 (H1N1), A/FM/1/47 (H1N1), A/PR8/34 (H1N1), A/New Caledonia/20/99 (H1N1), A/Solomon Island/3/06, A/Brisbane/59/07 (H1N1), A/Brisbane/10/07 (H3N2). Vaccines tested included the 2006/7 vaccine from Chiron Vaccines Limited (Liverpool, UK) and the 2008/9 formulation from Sanofi Pasteur Inc. (Swiftwater, Pa.). Recombinant HA proteins were provided by the influenza reagent resource (IRR; influenza reagent resource.org) of the CDC (recombinant HA from A/California/04/2009 (H1N1) (#FR-180), A/Brisbane/10/2007 (H1N1) (#FR-61), A/Brisbane/59/2007 (H3N2) (#FR-65)) or by Biodefense & Emerging Infections research repository (BEI; www.beiresources.org (recombinant HA from A/Indonesia/05/2005 (H5N1). A/Brevig Mission/1/1918 (H1N1) was purchased from SinoBiologicals.

ELISPOT Assay:

Direct ELISPOT to enumerate the number of either total IgG secreting, pandemic H1N1 influenza specific or vaccine specific ASC present in the PBMC samples were essentially done as previously described (Crotty et al., 2003). Briefly, 96-well ELISPOT filter plates (Millipore, MAHA N4510) were coated overnight with either the optimized amounts of purified pandemic H1N1 virions, recombinant HA from the pandemic H1N1 (as above), the 08/09 influenza vaccine at a dilution of 1/20 in PBS or with goat anti-human Ig (Caltag). Plates were washed and blocked by incubation with RPMI containing 10% FCS at 37° C. for 2 hrs. Purified and extensively washed PBMCs or sorted ASCs were added to the plates in dilution series and incubated for 6 hrs. Plates were washed with PBS followed by PBS containing 0.05% Tween and then incubated with a biotinylated anti-huIgG (gamma) antibody (Caltag) and incubated for 1.5 hrs at room temperature. After washing, the plates were incubated with an avidin-D-HRP conjugate (Vector Laboratories) and finally developed using AEC substrate (3 amino-9 ethyl-carbozole, Sigma). Developed plates were scanned and analyzed using an automated ELISPOT counter (Cellular Technologies Ltd.).

Flow Cytometry Analysis and Cell Sorting:

Analytical flow cytometry analysis was performed on whole blood following lysis of erythrocytes and fixing in 2% PFA. All live cell sorting and single cell sorting was performed on purified PBMCs using either a FACSVantage or ARIAII cell sorter system. All antibodies for both analytical and cell sorting cytometry were purchased from Pharmingen, except anti-CD27 that was purchased from eBiosciences. Anti-CD3-PECy7 or PerCP, anti-CD20-PECy7 or PerCP, anti-CD38-PE, anti-CD27-APC and anti-CD19-FITC. ASCs were gated and isolated as $CD19^+CD3^-CD20^{lo/-}CD27^{high}CD38^{high}$ cells. Flow cytometry data was analyzed using FlowJo software.

Generation of mAbs:

Identification of antibody variable region genes were done essentially as previously described (Smith et al., 2009; Wardemann et al., 2003; Wrammert et al., 2008). Briefly, single ASCs were sorted into 96-well PCR plates containing RNase inhibitor (Promega). VH and Vκ genes from each cell were amplified by RT-PCR and nested PCR reactions using cocktails of primers specific for both IgG and IgA using primer sets detailed in (Smith et al., 2009) and then sequenced. To generate recombinant antibodies, restriction sites were incorporated by PCR with primers to the particular variable and junctional genes. VH or Vκ genes amplified from each single cell were cloned into IgG1 or Igκ expression vectors as previously described (Smith et al., 2009; Wardemann et al., 2003; Wrammert et al., 2008). Antibody sequences are deposited on Genebank (Accession numbers: HQ689701-HQ689792). Heavy/light chain plasmids were co-transfected into the 293A cell line for expression and antibodies purified with protein A sepharose. Antibody proteins generated in this study can be provided in limited quantities upon request.

Mutational Analysis:

Antibody anti-H1N1 induced plasmablast variable genes were amplified by single cell RT-PCR using primer sets and PCR conditions that were previously published (Smith et al., 2009; Wrammert et al., 2008). Variable genes were determined using in house analysis software compared to the Immunogentics V gene data set and the IMGT search engine (Ehrenmann et al., 2010; Lefranc et al., 2009). Background mutation rates by this method is approximately 1 base-exchange per 1,000 bases sequenced (based on sequences of constant region gene segments). Comparisons were made to historical data some of which was previously published (Duty et al., 2009; Wrammert et al., 2008; Zheng et al., 2005).

Plaque Assay and PRNT$_{50}$ Assay:

MDCK cells were grown in 6-well plates at a density of 8×10$^5$/well. On the next day, cells were washed with PBS. Ten fold dilutions of virus were added in 500 ul DMEM and incubated at 37 C for 1 hour with mixing every 10 minutes. Cells were washed with PBS and overlayed with 199 media containing 0.5% agarose (Seakem), 1× antibiotics (100 U/ml penicillin, 100 mg/ml streptomycin), 0.2% BSA (Sigma-Aldrich) and 0.5 ug/ml TPCK-Trypsin (Sigma-Aldrich). Cells were incubated for 36-40 hrs and fixed with 2% PFA for 10 minutes. Agarose plugs were removed and cells were stained with 0.1% crystal violet in 25% EtOH for 1 min. After removal the crystal violet solution, plates were dried and used to count plaques in each well. For PRNT$_{50}$ assay, MDCK cells were prepared as above. On the next day, mAbs were 3 fold-diluted (60 to 0.74 ug/ml). 100 PFU of virus in 250 ul DMEM were incubated with equal volume of diluted mAbs at 37 C for 1 hour prior to the plaque assay as described above. Plaques were counted and the final concentration of antibodies that reduced plaques to below 50 PFU were scored as PRNT$_{50}$.

Determination of 50% Tissue Culture Infectious Dose (TCID50) and Microneutralization:

To determine the TCID$_{50}$, MDCK cells were grown in 96-well plate at a density of 1.5×10$^4$/well. On the next day, cells were washed with PBS and 10 fold-diluted viruses in 100 ul DMEM were added into each well and incubated at 37 C for 1 hour. After the incubation, cells were washed with PBS and 100 ul of DMEM containing 1× antibiotics (100 U/ml penicillin, 100 mg/ml streptomycin), 0.5% BSA (Sigma-Aldrich) and 0.5 ug/ml TPCK-Trypsin (Sigma-Aldrich) were added. Cells were further incubated for 60 hrs and 50 ul of the supernatant was incubated with equal volume of 0.5% of PBS-washed Turkey red blood cells (Rockland Immunochemicals) for 30 min. Four replicates were performed for each dilution and complete agglutination was scored as HA positive. Virus titers were calculated by Reed-Muench method. For microneutralization assay, 100 TCID$_{50}$ of virus in 50 ul DMEM were incubated with 50 ul of 3 fold-diluted antibodies (60 to 0.082 ug/ml) at 37 C for 1 hour. Cells were washed and incubated in the media as described above for 60 hrs. The microneutralization titer was determined as the final concentration of mAbs that completely inhibited infection.

HAI and ELISA Assays:

Whole virus, recombinant HA or vaccine-specific ELISA was performed on starting concentrations of 10 ug/ml of virus or recombinant HA and on 1:20 dilution of the vaccine as previously described (Wrammert et al., 2008). Briefly, microtiter plates were coated with live virus strains totaling 8 HAU of total virus per well or with 1 ug/ml of recombinant HA protein. In order to standardize the various ELISA assays common high affinity antibodies with similar affinities and binding characteristics against each virus strain were included on each plate and the plate developed when the absorbance of these controls reach 3.0±0.1 OD units. Goat anti-human IgG (Goat anti-human I-peroxidase-conjugate (Jackson ImmunoResearch, West Grove, Pa.) was used to detect binding of the recombinant antibodies followed by development with horseradish peroxidase substrate (BioRad, Hercules, Calif.). Absorbencies were measured at OD415 on a microplate reader (Molecular Devices, Sunnyvale, Calif). Affinity estimates were calculated by nonlinear regression analysis of curves from 8 dilutions of antibody (10 to 0.125 ug/ml) using GraphPad Prism. The hemagglutination inhibition (HAI) titers were determined as previously described (Wrammert et al., 2008). Briefly, the samples were then serially diluted with PBS in 96 well v-bottom plates and 8 HAU (as determined by incubation with 0.5% turkey RBCs in the absence of serum) of live egg-grown virus was added to the well. After 30 minutes at room temperature, 50 ul of 0.5% turkey RBCs (Rockland Immunochemicals) suspended in PBS with 0.5% BSA was added to each well and the plates were shaken manually. After an additional 30 minutes at room temperature, the serum titers or minimum effective concentrations were read based on the final dilution for which a button was observed.

Competition ELISA:

Competition ELISA was performed by inhibiting binding of each biotinylated antibody (NHS-coupled, Thermo Scientific) at the half-maximal binding concentration with a 10-fold molar excess of purified antibody. All comparisons of different antibodies were based on percentage absorbance values for each antibody against itself (which was scored as 100% inhibition). Detection was using streptavidin-HRP as described above for ELISA.

FACS analysis of binding of anti-HA antibodies with H5 and it's mutants as previously described (Sui et al., 2009): The full length HA gene (H5-TH04) of A/Thailand/2(SP-33)/2004 (H5N1) were codon-optimized for eukaryotic cell expression and cloned into pcDNA3.1 vector to obtain the pcDNA3.1-H5-TH04 construct (Sui et al., 2009). All mutants of H5-TH04 were derived from pcDNA3.1-H5-TH04 and constructed by the QuikChange method (Stratagene, La Jolla, Calif.). The full-length wild type H5-TH04 and mutants expressing plasmids were transfected transiently into 293T cells with Lipofectamine 2000 (Invitrogen Life Science). 24 h after transfection, cells were harvested for immunostaining. Anti-HA antibodies, or a control human mAb 80R (Sui et al., 2004) at 10 μg/mL or ferret anti-H5N1 serum at 1:300 dilution were incubated with transfected 293T cells at 4° C. for 1 h. Cells were then washed three times with PBS containing 0.5% BSA and 0.02% NaN$_3$. FITC-labeled goat anti-human IgG (Pierce Biotech., Rockford, Ill.) or FITC-labeled goat anti-ferret IgG (Bethyl, Montgomery, Tex.) were then added to cells and incubated for 30 minutes at 4° C. Cells were washed as above, and binding of antibodies to cells was analyzed using a Becton Dickinson FACScalibur with CellQuest software.

BIACORE Analysis:

The kinetic interactions of the mAbs with recombinant A/Cal/04/09 (H1N1) HA protein were determined by surface plasmon resonance (SPR) using a BIAcore3000 instrument. EM4C04 and SF1009-3F01 antibodies were immobilized at 10 ulmin$^{-1}$ on a CM5 sensor chip by amine coupling and recombinant HA at concentrations ranging from 0.5 nM to 15 nM in HBS-EP buffer were injected at 20 ulmin$^{-1}$ over the immobilized antibodies or reference cell surface. Running buffer (HBS-EP) was then applied for 600 s after which the sensor surface was regenerated by a single injection of 25 mM NaOH at 100 ulmin$^{-1}$. For the other experiments, recombinant HA (His-tagged) was immobilized at 5 ulmin$^{-1}$ on NTA sensor chips with a influenza density of 350 response units and the antibodies at concentrations ranging from 1 nM to 30 nM in HBS-P buffer were injected at 20 ulmin$^{-1}$ over the immobilized recombinant HA or reference cell surface, followed by a 600 s dissociation phase. All experiments were performed in triplicates. For kinetic analysis, injections over reference cell surface and injections with buffer were subtracted from the data. Association rates ($k_a$), dissociation rates ($k_d$) and equilibrium dissociation constants ($K_D$) were calculated by aligning the curves to fit a 1:1 binding model using BIAevaluation 4.1 software. Antibodies 1009-3B06, 1000-3E01, and 1000-2G06 could not be determined because these mAbs did not bind to the recombinant HA protein from baculovirus sufficiently well for SPR. Avidities for these mAbs and for the antibodies that did not neutralize infection in vitro were estimated by Scatchard plot analyses of ELISA data (shown in parentheses).

In Vivo Protection Experiments:

Female Balb/c mice 6-8 weeks old were used for the challenge studies. Mice were inoculated intra-nasally with 3×LD50 of a highly pathogenic, mouse-adapted pandemic H1N1 influenza virus (A/California/04/09), or PR/8/34 or FM/1/47 influenza virus. The mouse adapted pandemic H1N1 virus had been serially passaged in mice for five generations prior to use herein. The LD50 for all the viruses was determined by in vivo infection at various virus concentrations, according to the method of Reed and Muench. The experiments were conducted in accordance with ethical procedures and policies approved by the Emory University's Institutional Animal Care and Use Committee. In order to determine the prophylactic efficacy of the mAb, mice were treated intraperitoneally with 200 ug (10 mg/kg of body weight) of the specific mAbs. Twelve hours later mice were challenged with 3×LD50 of one of the mouse adapted influenza viruses used in the study. All mice were monitored daily for any signs of morbidity and mortality. Body weight changes were registered daily for a period of 14 days. All mice that lost more than 25% of their initial body weight were sacrificed according to the IACUC guideless. In order to determine the therapeutic efficacy of the mAbs, mice were challenged with 3×LD50 of the mouse-adapted pandemic H1N1 virus. At various times post infection (12, 24, 36, 48, 60 and 72 hours) mice were treated intraperitoneally with 200 □g (10 mg/kg of body weight) of the specific mAbs. All mice were monitored daily and the body weight changes were registered daily as described above.

Statistical Analysis:

Data was collected and graphed using MS Excel and Graphpad Prism software. Efficacy of the therapeutic and challenge experiments was evaluated by ANOVA using Graphpad Prism software.

Discussion

Our findings provide insight into the human B cell responses to a pandemic influenza virus strain. The unique genetic composition of the pandemic H1N1 influenza virus meant that our relatively young cohort probably had little or no pre-existing specific antibody mediated immunity to this virus prior to infection (Brockwell-Staats et al., 2009; Dawood et al., 2009; Garten et al., 2009; Hancock et al., 2009). Thus, two sources of B cells could have contributed to this response: newly recruited naïve B cells, and pre-existing memory B cells that bound to epitopes conserved between past seasonal strains and the pandemic H1N1 strain. We theorize that predominant activation of the latter, pre-existing memory cells, can account for the observed high frequency of neutralizing antibodies (11/15 HA-binding antibodies), the majority (9/11) of which are cross-reactive with seasonal H1N1 strains (FIG. 3C) and other group 1 influenza strains, including H5 HA. A number of observations support this conjecture.

Most convincingly, there was a particularly high frequency of cross-reactive antibodies overall, with a high level of somatic mutations found particularly amongst the variable genes of cross-reacting cells (FIG. 2 and FIG. 9). In fact, by ELISA most antibodies were cross-reactive and one third of the antibodies bound to past annual viral antigens at lower concentrations, suggesting higher avidity to past influenza strains than to the current pandemic H1N1 virus. Further, cross-reacting cells that bind with higher affinity to the pandemic H1N1 strain also have the highest frequency of variable-gene mutations (FIG. 9B). Antibodies that were broadly cross-reactive were amongst the more highly mutated clones (FIG. 9B). We propose that many of these cells were specific for cross-reactive epitopes present in annual influenza strains that then underwent further affinity maturation and adaptation to the infecting pandemic H1N1 virus. Supporting this conjecture, Corti et al. first demonstrated that naturally occurring HA-stalk reactive memory B cells could be isolated from the blood of people recently immunized with the annual vaccine, prior to the outbreak of pandemic H1N1 (Corti et al., 2010). The nature of that study was to screen EBV-transformed memory cell lines, thus precluding the determination of precise frequencies of these stalk-reactive B cells. However, these antibodies were estimated to be quite rare; occurring at 1 in thousands to 1 in hundreds of influenza-binding B cells, varying by individual. In contrast we show that plasmablasts activated by infection with the highly novel pandemic H1N1 influenza strain have substantially increased influenzaing to the HA-stalk region epitopes, totaling 10% of all influenza specific antibodies and half of the neutralizing antibodies (FIG. 4). In fact most specific antibodies isolated in this study were cross-reactive to past influenza strains. Collectively, the data described supports a model in which divergent viruses that are conserved only at the most critical regions for function will elicit a higher proportion of cross-reactive and neutralizing antibodies. Thus although the activated plasmablasts of relatively few patients could be analyzed in detail at the monoclonal antibody level, we proffer that with the proper immunogen, the long-sought development of a pan-influenza vaccine might be possible.

Interestingly, the highly specific antibody EM-4C04 was derived from a patient that had a very severe disease course, with persistent viral shedding over several weeks. In addition, the variable genes from the plasmablasts of this patient had the lowest average number of somatic mutations (FIG. 2B, outlier, and FIG. 9B). Taken together the unique specificity against pandemic H1N1, the low levels of somatic mutation, and the unusually severe disease in the absence of pre-disposing conditions suggest that this patient may have mounted a primary immune response to the pandemic H1N1 influenza infection. The complete lack of pre-existing immunity may have contributed to the more severe disease observed in this patient. In contrast, the activation of broadly cross-neutralizing memory B cells in those with immune experience to annual strains might have contributed to the less severe disease of most infected patients during the pandemic.

It is notable that there is a discrepancy between patients for serum MN titers, the severity of disease, and the frequency of plasmablasts expressing neutralizing antibodies (Table 1 and FIG. 3). For example, patient EM described above, despite having the worst disease course, had the greatest HAI and MN serum titers. This may be due to either the time from infection (day 31), allowing full seroconversion, or due to the presence of highly potent antibodies such as EM-4C04 whose activity was less likely to titer out. The highly specific nature of the response from this patient may have contributed to this advantage, ultimately better influenzaing the epitopes of the pandemic H1N1 strain. In contrast, patient 1009 had relatively low HAI and MN serum titers but the highest frequency of broadly neutralizing antibodies and a less severe disease course. One possibility is that our sampling from this patient was done prior to peak serological responses. Another possibility is that the high frequency of these potent antibodies in the memory B cell compartment may have resulted in rapid resolution of infection, precluding the development of a high serological response. A third possibility is that despite broader protection, the stalk-reactive antibodies are on the whole less potent and more rapidly titrated out then the highly specific antibodies to the HA-globular head. These various possibilities will be of significant interest to study in the future.

Finally, we report the development of a large panel of human mAbs induced by pandemic H1N1 infection. Prophylactic therapy with polyclonal or mAbs has successfully been used for RSV, rabies, Hepatitis A and B and varicella. In the case of influenza, mAbs have been shown to provide prophylactic or therapeutic protection in mice and other animal models (Palladino et al., 1995; Renegar et al., 2004; Reuman et al., 1983; Sweet et al., 1987). Also passive transfer of maternal antibodies in humans has been shown to confer protection (Puck et al., 1980). Several of the antibodies we isolated have broad neutralization capacity in vitro against divergent influenza strains and show potent prophylactic and therapeutic activity when used to treat mice that were lethally infected with influenza. These antibodies could provide much needed pandemic therapeutics to treat severe cases of influenza and to protect high-risk populations.

In conclusion, analyses of 46 mAbs induced by pandemic H1N1 infection indicated frequent activation of broadly-reactive B cells. We propose that these cells had a memory cell origin due to cross-reactivity to conserved and functionally important epitopes. If true then it will be important to characterize the efficacy of the pandemic H1N1 vaccine to induce a similarly cross-protective response.

---

What is claimed is:

1. A non-naturally occurring chimeric antibody, wherein the antibody-binds to an HA domain of influenza virus, having a heavy chain with a constant domain (CH) and variable domain (VH), and light chain with a variable domain (VL) and constant domain (CL) and comprises,
   (a) a VH CDR1 having an amino acid sequence identical to SEQ ID NO. 28;
   (b) a VH CDR2 having an amino acid sequence identical to SEQ ID NO. 32;
   (c) a VH CDR3 having an amino acid sequence identical to SEQ ID NO. 36;
   (d) a VL CDR1 having an amino acid sequence identical to SEQ ID NO. 29;
   (e) a VL CDR2 having an amino acid sequence Ala Ala Ser; and
   (f) a VL CDR3 having an amino acid sequence identical to SEQ ID NO. 37.

2. The non-naturally occurring chimeric antibody of claim 1, wherein the VH and VL respectively are selected from SEQ ID NO: 22 and SEQ ID NO: 23.

3. The non-naturally occurring chimeric antibody of claim 1, wherein the antibody binds H1N1 and H5N1.

4. The non-naturally occurring chimeric antibody of claim 1, wherein the antibody binds to the HA of two or more strains of H1N1.

5. The non-naturally occurring chimeric antibody of claim 1, wherein the antibody binds to the HA of two or more strains of H5N1.

* * * * *

SEQUENCE LISTING

```
<160> NUMBER OF SEQ ID NOS: 43

<210> SEQ ID NO 1
<211> LENGTH: 8
<212> TYPE: PRT
<213> ORGANISM: Homo sapiens

<400> SEQUENCE: 1

Gly Met Thr Ser Asn Ser Leu Ala
1               5

<210> SEQ ID NO 2
<211> LENGTH: 8
<212> TYPE: PRT
<213> ORGANISM: Homo sapiens

<400> SEQUENCE: 2

Ile Ile Pro Val Phe Glu Thr Pro
1               5

<210> SEQ ID NO 3
<211> LENGTH: 16
<212> TYPE: PRT
<213> ORGANISM: Homo sapiens

<400> SEQUENCE: 3

Ala Thr Ser Ala Gly Gly Ile Val Asn Tyr Tyr Leu Ser Phe Asn Ile
1               5                   10                  15

<210> SEQ ID NO 4
<211> LENGTH: 97
<212> TYPE: PRT
<213> ORGANISM: Homo sapiens

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Met Thr Ser Asn Ser Leu
            20                  25                  30

Ala Ile Ser Trp Val Arg Gln Ala Pro Gly Gln Gly Leu Glu Trp Met
        35                  40                  45

Gly Gly Ile Ile Pro Val Phe Glu Thr Pro Lys Tyr Ala Gln Lys Phe
    50                  55                  60

Gln Gly Arg Val Thr Ile Thr Ala Asp Lys Ser Thr Asn Thr Ala Tyr
65                  70                  75                  80
```

```
Met Asp Leu Ile Ser Leu Lys Ser Glu Asp Thr Ala Met Tyr Tyr Cys
                85                  90                  95

Ala

<210> SEQ ID NO 5
<211> LENGTH: 6
<212> TYPE: PRT
<213> ORGANISM: Homo sapiens

<400> SEQUENCE: 5

Gln Thr Ile Thr Thr Trp
1               5

<210> SEQ ID NO 6
<211> LENGTH: 9
<212> TYPE: PRT
<213> ORGANISM: Homo sapiens

<400> SEQUENCE: 6

Gln Gln Tyr Ser Thr Tyr Ser Gly Thr
1               5

<210> SEQ ID NO 7
<211> LENGTH: 94
<212> TYPE: PRT
<213> ORGANISM: Homo sapiens

<400> SEQUENCE: 7

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Thr Thr Trp
            20                  25                  30

Leu Ala Trp Tyr Gln Gln Lys Pro Gly Gln Ala Pro Lys Leu Leu Ile
        35                  40                  45

His Lys Thr Ser Thr Leu Glu Thr Gly Val Pro Ser Arg Phe Ser Gly
    50                  55                  60

Ser Gly Ser Gly Thr Gln Phe Thr Leu Thr Ile Thr Asn Leu Gln Pro
65                  70                  75                  80

Asp Asp Ser Ala Thr Tyr Tyr Cys Gln Gln Tyr Ser Thr Tyr
                85                  90

<210> SEQ ID NO 8
<211> LENGTH: 8
<212> TYPE: PRT
<213> ORGANISM: Homo sapiens

<400> SEQUENCE: 8

Gly Gly Thr Ser Asn Asn Tyr Pro
1               5

<210> SEQ ID NO 9
<211> LENGTH: 8
<212> TYPE: PRT
<213> ORGANISM: Homo sapiens

<400> SEQUENCE: 9

Ser Ile Pro Ile Phe Asn Thr Pro
1               5

<210> SEQ ID NO 10
<211> LENGTH: 16
```

```
<212> TYPE: PRT
<213> ORGANISM: Homo sapiens

<400> SEQUENCE: 10

Ala Thr Ser Ala Gly Gly Ile Val Asn Tyr Phe Leu Leu Phe Asp Ile
1               5                   10                  15

<210> SEQ ID NO 11
<211> LENGTH: 97
<212> TYPE: PRT
<213> ORGANISM: Homo sapiens

<400> SEQUENCE: 11

Gln Val Gln Leu Val Gln Ser Gly Ala Glu Leu Lys Lys Pro Gly Ser
1               5                   10                  15

Ser Val Lys Val Ser Cys Lys Thr Ser Gly Gly Thr Ser Asn Asn Tyr
            20                  25                  30

Pro Ile Ser Trp Val Arg Gln Ala Pro Gly Gln Gly Leu Glu Trp Met
        35                  40                  45

Gly Gly Ser Ile Pro Ile Phe Asn Thr Pro Lys Tyr Gly Lys Lys Phe
    50                  55                  60

Gln Gly Arg Val Thr Ile Thr Ser Asp Thr Ser Thr Ser Thr Ala Tyr
65                  70                  75                  80

Met Glu Leu Ser Ser Leu Arg Ser Asp Asp Thr Ala Ile Tyr Tyr Cys
                85                  90                  95

Ala

<210> SEQ ID NO 12
<211> LENGTH: 6
<212> TYPE: PRT
<213> ORGANISM: Homo sapiens

<400> SEQUENCE: 12

Gln Ser Ile Ser Asp Trp
1               5

<210> SEQ ID NO 13
<211> LENGTH: 9
<212> TYPE: PRT
<213> ORGANISM: Homo sapiens

<400> SEQUENCE: 13

Gln His Tyr Asn Thr Tyr Ser Gly Thr
1               5

<210> SEQ ID NO 14
<211> LENGTH: 94
<212> TYPE: PRT
<213> ORGANISM: Homo sapiens

<400> SEQUENCE: 14

Asp Ile Gln Met Thr Gln Ser Pro Ser Thr Leu Ser Ala Ser Val Gly
1               5                   10                  15

Asp Arg Val Thr Ile Ala Cys Arg Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

His Lys Ala Ser Ser Leu Glu Ser Gly Val Pro Ser Arg Phe Ser Gly
    50                  55                  60

Gly Gly Ser Gly Thr Glu Phe Thr Leu Thr Ile Ser Ser Leu Gln Ala
```

```
                     65                  70                  75                  80
Asp Asp Ser Ala Thr Tyr Tyr Cys Gln His Tyr Asn Thr Tyr
                 85                  90
```

<210> SEQ ID NO 15
<211> LENGTH: 8
<212> TYPE: PRT
<213> ORGANISM: Homo sapiens

<400> SEQUENCE: 15

```
Gly Gly Ile Phe Arg Ser Asn Ala
1               5
```

<210> SEQ ID NO 16
<211> LENGTH: 8
<212> TYPE: PRT
<213> ORGANISM: Homo sapiens

<400> SEQUENCE: 16

```
Ile Ile Ala Val Phe Gly Thr Ala
1               5
```

<210> SEQ ID NO 17
<211> LENGTH: 14
<212> TYPE: PRT
<213> ORGANISM: Homo sapiens

<400> SEQUENCE: 17

```
Ala Arg Gly Pro Tyr Tyr Tyr Gly Asn Ser His Leu Asp Phe
1               5                   10
```

<210> SEQ ID NO 18
<211> LENGTH: 97
<212> TYPE: PRT
<213> ORGANISM: Homo sapiens

<400> SEQUENCE: 18

```
Gln Val Gln Leu Val Gln Ser Gly Ala Glu Val Lys Lys Pro Gly Ser
1               5                   10                  15

Ser Val Lys Val Ser Cys Arg Ala Ser Gly Ile Phe Arg Ser Asn
                20                  25                  30

Ala Ile Ser Trp Val Arg Gln Ala Pro Gly Gln Gly Leu Glu Trp Met
            35                  40                  45

Gly Glu Ile Ile Ala Val Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala
```

<210> SEQ ID NO 19
<211> LENGTH: 7
<212> TYPE: PRT
<213> ORGANISM: Homo sapiens

<400> SEQUENCE: 19

```
Gln Ser Val Ser Ser Asn Tyr
1               5
```

<210> SEQ ID NO 20

-continued

```
<211> LENGTH: 9
<212> TYPE: PRT
<213> ORGANISM: Homo sapiens

<400> SEQUENCE: 20

Gln Gln Tyr Gly Thr Ser Pro Arg Thr
1               5

<210> SEQ ID NO 21
<211> LENGTH: 96
<212> TYPE: PRT
<213> ORGANISM: Homo sapiens

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Ala Ile Ser Arg Leu Glu
65                  70                  75                  80

Pro Glu Asp Phe Ala Val Tyr Tyr Cys Gln Gln Tyr Gly Thr Ser Pro
                85                  90                  95

<210> SEQ ID NO 22
<211> LENGTH: 121
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn Phe
            20                  25                  30

Ala Val Ser Trp Val Arg Gln Ala Pro Gly Gln Gly Pro Glu Trp Met
        35                  40                  45

Gly Gly Ile Ile Ala Ile Phe Gly Thr Ala Lys Tyr Ala Gln Lys Phe
    50                  55                  60

Gln Gly Arg Val Thr Ile Ser Ala Asp Glu Ser Thr Arg Ile Val Gln
65                  70                  75                  80

Met Glu Leu Ser Ser Leu Arg Ser Asp Asp Thr Ala Ile Tyr Tyr Cys
                85                  90                  95

Ala Ser Ser Gly Ser Tyr Tyr Gly Asp Tyr Phe Asp Tyr Trp Gly
            100                 105                 110

Gln Gly Thr Leu Val Thr Val Ser Ser
        115                 120

<210> SEQ ID NO 23
<211> LENGTH: 107
<212> TYPE: PRT
<213> ORGANISM: Homo sapiens

<400> SEQUENCE: 23

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
```

```
                    20                  25                  30

Leu Ala Trp Tyr Gln Gln Thr Pro Gly Gln Ala Pro Arg Leu Leu Ile
            35                  40                  45

Tyr Ala Ala Ser Ser Arg Ala Thr Gly Ile Pro Ala Arg Phe Ser Gly
 50                  55                  60

Ser Gly Ser Gly Thr Glu Phe Thr Leu Ser Ile Ser Ser Leu Gln Pro
 65                  70                  75                  80

Glu Asp Phe Ala Val Tyr Tyr Cys Gln Gln Tyr Asn Asn Trp Pro Arg
                 85                  90                  95

Thr Phe Gly Gln Gly Thr Lys Val Glu Ile Lys
                100                 105

<210> SEQ ID NO 24
<211> LENGTH: 97
<212> TYPE: PRT
<213> ORGANISM: Homo sapiens

<400> SEQUENCE: 24

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Arg Asn Phe
                20                  25                  30

Ala Val Ser Trp Val Arg Gln Ala Pro Gly Gln Gly Pro Glu Trp Met
            35                  40                  45

Gly Gly Ile Ile Ala Ile Phe Gly Thr Ala Lys Tyr Ala Gln Lys Phe
 50                  55                  60

Gln Gly Arg Val Thr Ile Ser Ala Asp Glu Ser Thr Arg Ile Val Gln
 65                  70                  75                  80

Met Glu Leu Ser Ser Leu Arg Ser Asp Asp Thr Ala Ile Tyr Tyr Cys
                 85                  90                  95

Ala

<210> SEQ ID NO 25
<211> LENGTH: 95
<212> TYPE: PRT
<213> ORGANISM: Homo sapiens

<400> SEQUENCE: 25

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Thr Pro Gly Gln Ala Pro Arg Leu Leu Ile
            35                  40                  45

Tyr Ala Ala Ser Ser Arg Ala Thr Gly Ile Pro Ala Arg Phe Ser Gly
 50                  55                  60

Ser Gly Ser Gly Thr Glu Phe Thr Leu Ser Ile Ser Ser Leu Gln Pro
 65                  70                  75                  80

Glu Asp Phe Ala Val Tyr Tyr Cys Gln Gln Tyr Asn Asn Trp Pro
                 85                  90                  95

<210> SEQ ID NO 26
<211> LENGTH: 25
<212> TYPE: PRT
<213> ORGANISM: Homo sapiens

<400> SEQUENCE: 26
```

-continued

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 27
<211> LENGTH: 26
<212> TYPE: PRT
<213> ORGANISM: Homo sapiens

<400> SEQUENCE: 27

Glu Ile Val Met Thr Gln Ser Pro Ala Thr Leu Ser Val Ser Pro Gly
1               5                   10                  15

Glu Arg Ala Thr Leu Ser Cys Arg Ala Ser
            20                  25

<210> SEQ ID NO 28
<211> LENGTH: 8
<212> TYPE: PRT
<213> ORGANISM: Homo sapiens

<400> SEQUENCE: 28

Gly Gly Thr Phe Arg Asn Phe Ala
1               5

<210> SEQ ID NO 29
<211> LENGTH: 6
<212> TYPE: PRT
<213> ORGANISM: Homo sapiens

<400> SEQUENCE: 29

Gln Ser Val Ser Ser Asn
1               5

<210> SEQ ID NO 30
<211> LENGTH: 17
<212> TYPE: PRT
<213> ORGANISM: Homo sapiens

<400> SEQUENCE: 30

Val Ser Trp Val Arg Gln Ala Pro Gly Gln Gly Pro Glu Trp Met Gly
1               5                   10                  15

Gly

<210> SEQ ID NO 31
<211> LENGTH: 17
<212> TYPE: PRT
<213> ORGANISM: Homo sapiens

<400> SEQUENCE: 31

Leu Ala Trp Tyr Gln Gln Thr Pro Gly Gln Ala Pro Arg Leu Leu Ile
1               5                   10                  15

Tyr

<210> SEQ ID NO 32
<211> LENGTH: 8
<212> TYPE: PRT
<213> ORGANISM: Homo sapiens

<400> SEQUENCE: 32

Ile Ile Ala Ile Phe Gly Thr Ala
1               5

```
<210> SEQ ID NO 33
<211> LENGTH: 3
<212> TYPE: PRT
<213> ORGANISM: Homo sapiens

<400> SEQUENCE: 33

Ala Ala Ser
1

<210> SEQ ID NO 34
<211> LENGTH: 38
<212> TYPE: PRT
<213> ORGANISM: Homo sapiens

<400> SEQUENCE: 34

Lys Tyr Ala Gln Lys Phe Gln Gly Arg Val Thr Ile Ser Ala Asp Glu
1               5                   10                  15

Ser Thr Arg Ile Val Gln Met Glu Leu Ser Ser Leu Arg Ser Asp Asp
            20                  25                  30

Thr Ala Ile Tyr Tyr Cys
        35

<210> SEQ ID NO 35
<211> LENGTH: 36
<212> TYPE: PRT
<213> ORGANISM: Homo sapiens

<400> SEQUENCE: 35

Ser Arg Ala Thr Gly Ile Pro Ala Arg Phe Ser Gly Ser Gly Ser Gly
1               5                   10                  15

Thr Glu Phe Thr Leu Ser Ile Ser Ser Leu Gln Pro Glu Asp Phe Ala
            20                  25                  30

Val Tyr Tyr Cys
        35

<210> SEQ ID NO 36
<211> LENGTH: 14
<212> TYPE: PRT
<213> ORGANISM: Homo sapiens

<400> SEQUENCE: 36

Ala Ser Ser Ser Gly Ser Tyr Tyr Gly Asp Tyr Phe Asp Tyr
1               5                   10

<210> SEQ ID NO 37
<211> LENGTH: 9
<212> TYPE: PRT
<213> ORGANISM: Homo sapiens

<400> SEQUENCE: 37

Gln Gln Tyr Asn Asn Trp Pro Arg Thr
1               5

<210> SEQ ID NO 38
<211> LENGTH: 16
<212> TYPE: PRT
<213> ORGANISM: Homo sapiens

<400> SEQUENCE: 38

Cys Ala Ser Ser Ser Gly Ser Tyr Tyr Gly Asp Tyr Phe Asp Tyr Trp
1               5                   10                  15
```

```
<210> SEQ ID NO 39
<211> LENGTH: 11
<212> TYPE: PRT
<213> ORGANISM: Homo sapiens

<400> SEQUENCE: 39

Cys Gln Gln Tyr Asn Asn Trp Pro Arg Thr Phe
1               5                   10

<210> SEQ ID NO 40
<211> LENGTH: 15
<212> TYPE: PRT
<213> ORGANISM: Homo sapiens

<400> SEQUENCE: 40

Tyr Phe Asp Tyr Trp Gly Gln Gly Thr Leu Val Thr Val Ser Ser
1               5                   10                  15

<210> SEQ ID NO 41
<211> LENGTH: 11
<212> TYPE: PRT
<213> ORGANISM: Homo sapiens

<400> SEQUENCE: 41

Thr Phe Gly Gln Gly Thr Lys Val Glu Ile Lys
1               5                   10

<210> SEQ ID NO 42
<211> LENGTH: 11
<212> TYPE: PRT
<213> ORGANISM: Homo sapiens

<400> SEQUENCE: 42

Trp Gly Gln Gly Thr Leu Val Thr Val Ser Ser
1               5                   10

<210> SEQ ID NO 43
<211> LENGTH: 10
<212> TYPE: PRT
<213> ORGANISM: Homo sapiens

<400> SEQUENCE: 43

Phe Gly Gln Gly Thr Lys Val Glu Ile Lys
1               5                   10
```